United States Patent
Liu et al.

(10) Patent No.: US 9,983,127 B2
(45) Date of Patent: May 29, 2018

(54) OPTICAL DETECTION DEVICE AND OPTICAL DETECTION METHOD

(71) Applicant: Nanyang Technological University, Singapore (SG)

(72) Inventors: Quan Liu, Singapore (SG); Yi Hong Ong, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days. days.

(21) Appl. No.: 14/475,853

(22) Filed: Sep. 3, 2014

(65) Prior Publication Data

US 2015/0062573 A1 Mar. 5, 2015

Related U.S. Application Data

(60) Provisional application No. 61/873,087, filed on Sep. 3, 2013.

(51) Int. Cl.
| | |
|---|---|
| G01J 3/00 | (2006.01) |
| G01N 21/47 | (2006.01) |
| A61B 5/00 | (2006.01) |
| G01N 21/64 | (2006.01) |
| G01N 21/65 | (2006.01) |
| G01N 21/17 | (2006.01) |

(52) U.S. Cl.
CPC ......... G01N 21/474 (2013.01); A61B 5/0075 (2013.01); A61B 5/444 (2013.01); G01N 21/4795 (2013.01); G01N 21/645 (2013.01); G01N 21/6486 (2013.01); G01N 21/65 (2013.01); G01N 2021/1782 (2013.01); G01N 2021/4747 (2013.01); G01N 2021/4759 (2013.01); G01N 2201/0221 (2013.01)

(58) Field of Classification Search
CPC ........... G01N 21/4738; G01N 21/6486; G01N 21/474; G01N 21/4795; G01N 21/645; G01N 21/65; G01N 2021/1782; G01N 2021/4747; G01N 2021/4759; G01N 2021/0221; A61B 5/0075; A61B 5/444
USPC .................................................. 356/300–334
See application file for complete search history.

(56) References Cited

U.S. PATENT DOCUMENTS

| | | | |
|---|---|---|---|
| 2003/0091307 A1* | 5/2003 | Hurley et al. | 385/109 |
| 2009/0097007 A1* | 4/2009 | Tanaka | 355/67 |
| 2010/0302396 A1* | 12/2010 | Golub et al. | 348/222.1 |

(Continued)

OTHER PUBLICATIONS

Allen-Hoffmann, B. L. et al., *Normal Growth and Differentiation in a Spontaneously Immortalized Near-Dipload human Keratinocyte Cell Line, NIKS*, The Society for Investigative Dermatology, Inc. (2002) 444-455.

(Continued)

*Primary Examiner* — Hina F Ayub
(74) *Attorney, Agent, or Firm* — Alston & Bird LLP

(57) ABSTRACT

According to embodiments of the present invention, an optical detection device is provided. The optical detection device includes an optics arrangement configured to generate an annular illumination pattern to illuminate a portion of a sample and further configured to receive a return light from the portion of the sample illuminated by the annular illumination pattern; and a detector arrangement configured to detect the return light. According to further embodiments of the present invention, an optical detection method is also provided.

17 Claims, 24 Drawing Sheets

(56) References Cited

U.S. PATENT DOCUMENTS

| | | | |
|---|---|---|---|
| 2011/0059016 A1* | 3/2011 | Ramanujam | A61B 5/0059 424/9.1 |
| 2011/0206234 A1* | 8/2011 | Benderly et al. | 382/100 |
| 2013/0083322 A1* | 4/2013 | Iketaki et al. | 356/301 |
| 2013/0236883 A1* | 9/2013 | Atrache et al. | 435/5 |
| 2014/0268104 A1* | 9/2014 | Treado et al. | 356/51 |
| 2014/0368817 A1* | 12/2014 | Xie et al. | 356/301 |
| 2015/0109618 A1* | 4/2015 | Howell et al. | 356/326 |

OTHER PUBLICATIONS

Andree, S. et al., *Evaluation of a Novel Noncontact Spectrally and Spatially Resolved Reflectance Setup With continuously Variable Source-Detector Separation Using Silicon Phantoms*, Journal of Biomedical Optics 15(6) 067009 (Nov./Dec. 2010) 1-12

Arifler, D. et al., *Reflectance Spectroscopy for Diagnosis of Epithelial Precancer: Model-Based Analysis of Fiber-Optic Probe Designs to Resolve Spectral Information From Epithelium and Stroma*, Applied Optics, vol. 44, No. 20 (Jul. 2005) 4291-4305.

Atecio, J. A. D. et al., *Influence of Probe Pressure of Human Skin Diffuse Reflectance Spectroscopy Measurements*, Optical Memory and Neural Networks (Information Optics), vol. 18, No. 1 (2009) 6-14.

Bish, S. F. et al., *Development of a Noncontact Diffuse Optical Spectroscopy Probe for Measuring Tissue Optical Properties*, Journal of Biomedical Optics, vol. 16(12) (Dec. 2011) 1-3.

Breunig, H. G. et al., *Multiphoton Excitation Characteristics of Cellular Fluorophores of Human Skin in vivo*, Optics Express, vol. 18, No. 8 (Apr. 2010) 7857-7871.

Brookner, C. et al., *Effects of Biographical Variables on Cervical Fluorescence Emission Spectra*, Journal of Biomedical Optics 8(3) (Jul. 2003) 479-483.

Chang, S. K. et al., *Analytical Model to Describe Fluorescence Spectra of Normal and Preneoplastic Epithelial Tissue: Comparison With Monte Carlo Simulations and Clinical Measurements*, Journal of Biomedical Optics 9(3) (May/Jun. 2004) 511-522.

Cubeddu, R. et al., *A Solid Tissue Phantom for Photon Migration Studies*, Phys. Med. Biol. 42 (1997) 1971-1979.

Ding, H. et al., *Determination of Refractive Indices of Porcine Skin Tissues and Intralipid at Eight Wavelengths Between 325 and 1557 nm*, J. Opt. Soc. Am. A, vol. 22, No. 6 (Jun. 2005) 1151-1157.

Drezek, R. et al., *Autofluorescence Microscopy of Fresh Cervical-Tissue Sections Reveals Alternations in Tissue Biochemistry With Dysplasia*, Photochemistry and Photobiology, 73(6) (2001) 636-641.

Drezek, R. et al., *Understanding the Contributions of NADH and collagen to Cervical Tissue Fluorescence Spectra: Modeling, Measurements, and Implications*, Journal of Biomedical Optics 6(4) (Oct. 2001) 385-396.

Everall, N. J., *Modeling and Measuring the Effect of Refraction on the Depth Resolution of Confocal Raman Microscopy*, Applied Spectroscopy, vol. 54, No. 6 (2000) 773-782.

Gill, E. M. et al., *Relationship Between Collgen Autofluorescence of the Human Cervix and Menopausal Status*, Photochemistry and Photobiology, 77(6) (2003) 653-658.

Hielscher, A. H. et al., *Diffuse Backscattering Mueller Matrices of Highly Scattering Media*, Optics Express, vol. 1, No. 13 (Dec. 1977) 441-453.

Kortun, C. et al., *Combined Monte Carlo and Finite-Difference Time-Domain Modeling for Biophotonic Analysis: Implications on Reflectance-Based Diagnosis of Epithelial Precancer*, Journal of Biomedical Optics 13(3) 034014 (May/Jun. 2008) 1-14.

Lim, L. et al., *Probe Pressure Effects on Human Skin Diffuse Reflectance and Fluorescence Spectroscopy Measurements*, Journal of Biomedical Optics, 16(1) 011012 (Jan. 2011) 1-9.

Lui, Q. et al., *Experimental Proof of the Feasibility of Using an Angled Fiber-Optic Probe for Depth-Sensitive Fluorescence Spectroscopy of Turbid Media*, Optics Letters, vol. 29, No. 17 (Sep. 2004) 2034-2036.

Lui, Q. et al., *Relationship Between Depth of a Target in a Turbid Medium and Fluorescence Measured by a Variable-Aperture Method*, Optics Letters, vol. 27, No. 2 (Jan. 2002) 104-106.

Liu, Q., *Role of Optical Spectroscopy Using Endogenous Contrasts in Clinical Cancer Diagnosis*, World J Clin Oncol (Jan. 2011) 50-63.

Liu, Q. et al., *Sequential Estimation of Optical Properties of a Two-Layered Epithelial Tissue Model from Depth-Resolved ultra-violet-visible Diffuse Reflectance Spectra*, Applied Optics, vol. 45, No. 19 (Jul. 2006) 4776-4790.

Mazurenka, M. et al., *Non-Contact Time-Resolved Diffuse Reflectance Imaging at Null Source-Detector Separation*, Optics Express, vol. 20, No. 1 (Jan. 2012) 283-290.

Michels, R. et al., *Optical Properties of Fat Emulsions*, Optics Express, vol. 16, No. 8 (Apr. 2008) 5907-5925.

Ong, Y. H. et al., *Axicon Lens-Based Cone Shell Configuration for Depth-Sensitive Fluorescence Measurements in Turbid Media*, Optics Letters, vol. 38, No. 15 (Aug. 2013) 2647-2649.

Ong, Y. H. et al., *Fast Depth-Sensitive Fluorescence Measurements in Turbid Media Using cone Shell Configuration*, Optical Society of America (2013) 1-4.

Pavlova, I et al., *Microanatomical and Biochemical Origins of Normal and Precancerous Cervical Autofluorescence Using Laser-Scanning Fluorescence Confocal Microscopy*, Photochemistry and Photobiology, 77(5) (2003) 550-555.

Pfefer, T. J. et al., *Selective Detection of Fluorophore Layers in Turbide Media: The Role of Fiber-Optical Probe Design*, Optics Letters, vol. 28, No. 2 (Jan. 2003) 120-122.

Phefer, T. J. et al., *Oblique-Incidence Illumination and Collection for Depth-Selective Fluorescence Spectroscopy*, Journal of Biomedical Optics 19(4) 044016(Jul./Aug. 2005) 1-9.

Qu, J. et al., *Optical Properties of Normal and Carcinomatous Bronchial Tissue*, Applied Optics, vol. 33, No. 31, (Nov. 1994) 7397-7405.

Radosevich, A. J. et al., *Measurement of the Spatial Backscattering Impulse-Response at Short Length Scales With Polarized Enhanced Backscattering*, Optics Letters, vol. 36, No. 24 (Dec. 2011) 4737-4739.

Reif, R. et al., *Analysis of Changes in Reflectance Measurements on Biological Tissues Subjects to Different Probe Pressures*, Journal of Biomedical Optics, vol. 13(1) (Jan. 2008), 1-3.

Salomatina, E. et al., *Optical Properties of Normal and Cancerous Human Skin in the Visible and Near-Infrared Spectral Range*, Journal of Biomedical Optics 11(6) 064026 (Nov./Dec. 2006) 1-9.

Schwarz, R. A. et al., *Autofluorescence and Diffuse Reflectance Spectroscopy of Oral Epithelial Tissue Using a Depth-Sensitive Fiber-Optic Probe*, Applied Optics, vol. 47, No. 6 (Feb. 2008) 825-834.

Sung, K-B. et al., *Enhancing the Sensitivity to Scattering Coefficient of the Epithelium in a Two-Layered Tissue Model by Oblique Optical Fibers: Monte Carlo Study*, Journal of Biomedical Optics, vol. 17(10) (Oct. 2012) 1-14.

Ti, Y. et al., *Effects of Probe Contact Pressure on in vivo Optical Spectroscopy*, Optics Express, vol. 16, No. 6 (Mar. 2008) 4250-4262.

Turzhitsky, V. et al., *Multiple Scattering Model for the Penetration Depth of Low-Coherence Enhanced Backscattering*, Journal of Biomedical Optics, vol. 16(9) (Sep. 2011) 1-5.

Utzinger, U. et al., *Fiber Optic Probes for Biomedical Optical Spectroscopy*, Journal of Biomedical Optics 8(1) (Jan. 2003) 121-147.

Vitkin, E. et al., *Photon Diffusion Near the Point-of-Entry in Anisotropically Scattering Turbid Media*, Nature Communications (Dec. 2011) 1-8.

Walker, D. C. et al., *A Study of the Morphological Parameters of Cervical Squamous Epithelium*, Physiol. Meas. 24 (2003) 121-135.

Wang, A. M. J. et al., *Depth-Sensitive Reflectance Measurements Using Obliquely Oriented Fiber Probes*, Journal of Biomedical Optics 10(4) 044017 (Jul./Aug. 2005) 1-17.

Wang, H-W. et al., *Diffuse Reflectance Spectroscopy Detects Increased Hemoglobin Concentration and Decreased Oxygenation During Colon Carcinogenesis From Normal to Malignant Tumors*, Optics Express, vol. 17, No. 4 (Feb. 2009) 2805-2817.

(56) References Cited

OTHER PUBLICATIONS

Wang, L. H. et al., *MCML—Monte-Carlo Modeling of Light Transport in Multi-layered Tissues*, Computer Methods and Program in Biomedicine 47 (1995) 131-146.
Wang, L. V. et al., *Absorption Distribution of an Optical Beam Focused Into a Turbid Medium*, Applied Optics, vol. 38, No. 22 (Aug. 1999) 4951-4958.
Zhu, C. et al., *Numerical Investigation of Lens Based Setup for Depth Sensitive Diffuse Reflectance Measurements in an Epithelial Cancer Model*, Optics Express, vol. 20, No. 28 (Dec. 2012) 29807-29822.
Zhu, C. et al., *Validity of the Semi-Infinite Tumor Model in Diffuse Reflectance Spectroscopy for Epithelial Cancer Diagnosis: a Monte Carlo Study*, Optics Express, vol. 19, No. 18 (Aug. 2011) 17799-17812.
Zonios, G. et al., *Diffuse Reflectance Spectroscopy of Human Adenomatous Colon Polyps in vivo*, Applied Optics, vol. 38, No. 31 (Nov. 1999) 6628-6637.
Schott Optical Glass Data Sheet (Dec. 2012) 125 pages.

\* cited by examiner

OPTICAL DETECTION DEVICE AND OPTICAL DETECTION METHOD

CROSS-REFERENCE TO RELATED APPLICATION

This application claims the benefit of priority of U.S. provisional application No. 61/873,087, filed 3 Sep. 2013, the content of it being hereby incorporated by reference in its entirety for all purposes.

TECHNICAL FIELD

Various embodiments relate to an optical detection device and an optical detection method.

BACKGROUND

Diffuse reflectance spectroscopy has been investigated for the early diagnosis of epithelial cancer. Due to its non-invasiveness and capability to provide quantitative information about the physiological and pathological status of tissues in real time, this technique of diffuse reflectance spectroscopy has significant potential to be widely used in clinical settings.

In a typical diffuse reflectance setup, a fiber-optic probe serves as the conduit for the delivery of illuminating light and collection of emitted light. The fiber-optic probe is a metal cylindrical tube enclosing one or multiple optical fibers, in which some fibers are used for delivering light onto a tissue surface and the same fibers or other fibers depending on the probe design are used for collecting light emanating from the tissue surface.

Although fiber-optic probes are widely used in optical spectroscopy due to their flexibility and high efficiency, the uncertainty in measurements due to inconsistent probe-sample pressure is difficult to remove. The inconsistent pressure may induce significant distortions in measured spectra, which may consequently cause large errors in diagnosis.

To reduce such an artifact, lens based setups for non-contact diffuse reflectance measurements have been explored. For example, a lens based setup involving a spherical and a flat folding mirror for illumination with two achromatic lenses for detection has been investigated. An illumination fiber is placed at the focal point of the spherical mirror to deliver the white light to a tissue surface. A detection fiber is placed at the focal point of the top achromatic lens to transmit diffusely scattered light to a spectrometer. The distance between the illumination and the detection area can be varied continuously; moreover, both source and detection fibers with different diameters can be used. Therefore, this non-contact lens based setup is able to perform spatially resolved diffuse reflectance measurements without physically contacting a tissue sample.

A different setup for non-contact diffuse reflectance measurements has also been proposed where two collimating lenses are used to image the illumination and collection fibers onto a tissue surface and serve as a non-contact probe to eliminate the influence of inconsistent probe-tissue pressure that may be present in a contact probe. A customized autofocus mechanism has been incorporated in the setup to address the limit of the lens in focal depth.

Further, a non-contact lens based setup for time-resolved diffuse reflectance measurements, in which laser scanning is used to achieve imaging, has been introduced.

Lens based setups have been demonstrated as promising tools for non-contact diffuse reflectance measurements without distortion due to inconsistent probe sample contact.

There also exists other techniques such as low coherence enhanced backscattering, diffuse backscattering, and confocal technique for non-contact diffuse reflectance measurements. The dependence of the penetration depth of low coherence enhanced backscattering signals on optical properties has been examined using Monte Carlo modeling, but the simulation of lens based illumination and detection has not been explored. In other words, there has been no report of Monte Carlo modeling of lens based non-contact setup for depth sensitive diffuse reflectance measurements.

Similar to diffuse reflectance spectroscopy, which involves the use of visible light, ultraviolet-visible fluorescence spectroscopy has also been widely explored in the detection of precancers in human epithelial tissues. Vital diagnostic information about morphological and biochemical changes can be extracted from various fluorophores present in epithelial tissues. Such autofluorescence spectroscopy offers a non-invasive and effective detection approach. However, the distribution, or more specifically, the depth distribution of endogenous fluorophores may be affected by the progression of the disease state and various other factors such as age and menopausal status.

A depth-sensitive probe that can measure fluorescence spectra as a function of depth enhances the diagnostic performance of this technique. Achieving high depth sensitivity to a specific subsurface region in human epithelial tissue is a great challenge as photons are quickly scattered when entering a tissue that is a diffusively scattering medium. Furthermore, the dominance of fluorescence signals from overlying layers significantly reduces the contrast of fluorescence signals originated from the subsurface region of interest, thus limiting the diagnostic performance of this technique.

Currently, depth-sensitive fluorescence measurements can be achieved in two approaches, namely the fiber optic-based contact setup and the lens-based noncontact setup.

Fiber optic setups achieve depth-sensitive measurements by varying the source-detector separation, aperture diameter, and/or angle of illumination and collection fibers.

Lens-based setups use a single lens or a combination of lenses to achieve a cone configuration, in which both the excitation and emission volumes form light cones in an optically transparent medium. One drawback of the lens-based setup is the limited sensitivity to fluorescence originating from sub-surface layers due to the contribution from shallower layers in a layered structure such as epithelial tissues.

There is therefore a need for an optical detection device and an optical detection method with improved depth sensitivity to deep layers of samples and without the need to perform alterations which may induce uncertainty in optical coupling and significant inconvenience in clinical measurements, thereby addressing at least one or more of the problems mentioned above.

SUMMARY

According to an embodiment, an optical detection device is provided. The optical detection device may include an optics arrangement configured to generate an annular illumination pattern to illuminate a portion of a sample and further configured to receive a return light from the portion of the sample illuminated by the annular illumination pattern; and a detector arrangement configured to detect the return light.

According to an embodiment, an optical detection method is provided. The method may include generating an annular illumination pattern; illuminating a portion of a sample with the annular illumination pattern; and detecting a return light from the portion of the sample illuminated by the annular illumination pattern.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may relate to depth sensitive optical measurements.

Various embodiments may relate to a numerical investigation of lens based setup for depth sensitive diffuse reflectance measurements in an epithelial cancer model.

Various embodiments may provide a handheld probe for depth sensitive optical measurements. For example, the handheld probe may be a portable probe.

Various embodiments may provide an axicon lens-based cone shell configuration for depth-sensitive fluorescence measurements in turbid media.

Various embodiments may provide fast depth-sensitive fluorescence measurements in turbid media using a cone shell configuration.

Figure 1A:
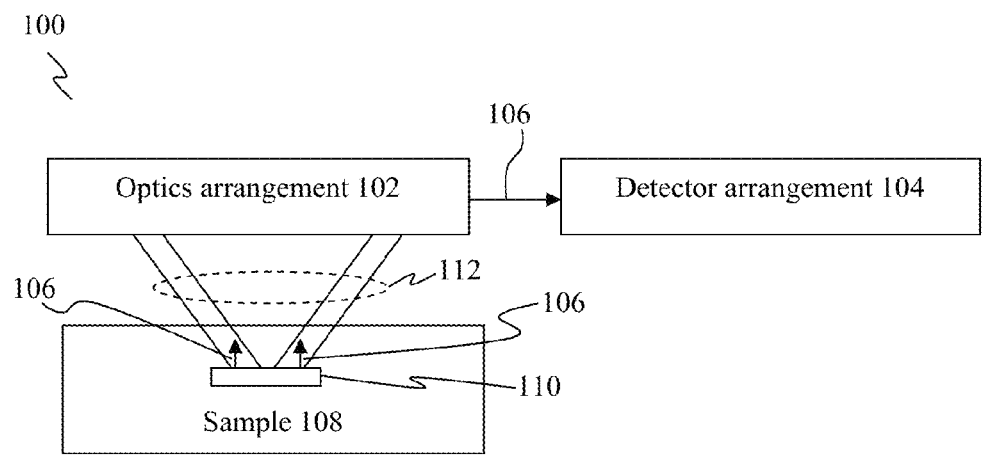
FIG. 1A shows a schematic view of an optical detection device, according to various embodiments.

FIG. 1A shows a schematic view of an optical detection device 100, according to various embodiments. The optical detection device 100 includes an optics arrangement 102 configured to generate an annular illumination pattern 112 to illuminate a portion 110 of a sample 108 and further configured to receive a return light 106 from the portion 110 of the sample 108 illuminated by the annular illumination pattern 112; and a detector arrangement 104 configured to detect the return light 106.

In other words, an optical detection device 100 may be provided. The optical detection device 100 may include an optics arrangement 102, which for example may have an assembly of optical elements. The optics arrangement 102 may be configured to generate an annular illumination pattern 112 (e.g. light having a ring radius and/or a ring thickness or a laser ring) to illuminate a portion 110 of a sample 108 (e.g. a tissue phantom or a tissue sample). It should be appreciated that the term "portion" in relation to a sample may include a point on the sample or within the sample. For example, the portion 110 of the sample 108 may be a sub-surface portion of the sample 108, e.g. within a thickness of the sample 108.

The optics arrangement 102 may further be configured to receive a return light 106 originating from the portion 110 of the sample 108 illuminated by the annular illumination pattern 112. The optics arrangement 102 may be further configured to re-direct the return light 106.

In various embodiments of the optical detection device 100, a detector arrangement 104 may be optically coupled to the optics arrangement 102 and may be configured to detect the return light 106.

In the context of various embodiments, for example, the return light 106 may include fluorescence or fluorescent light emitted or generated from the sample 108, or light reflected from the sample 108, or a Raman signal from the sample 108.

In the context of various embodiments, the term "annular" may mean ring-shaped. The ring may be a circular band or a non-circular band. For example, the term "annular" may be at least substantially elliptical or may be of any shape enclosed to include a hollow centre.

In various embodiments, the annular (or ring) illumination pattern 112 may form part of a cone shell illumination configuration.

In various embodiments, the annular (or ring) illumination pattern 112 may be focused towards a focal point within the thickness of the sample 108.

In various embodiments, the detector arrangement 104 may be configured to provide a measure or parameter of the return light 106, for example, the parameter may be in the form of intensity (e.g. fluorescence intensity).

In various embodiments, the optical detection device 100 may further include a processor configured to process the detected return light.

In various embodiments, the optics arrangement 102 may include shaping optics for receiving a light and shaping the light to generate the annular illumination pattern 112. For example, the light may be provided by a point source or may be collimated light.

In various embodiments, the shaping optics may include two axicon lenses to generate the annular illumination pattern 112. The two axicon lenses may further be configured to collimate the annular illumination pattern 112.

In the context of various embodiments, the term "axicon lens" may mean a type of lens which may have a conical surface. An axicon lens may image a point source into a line along the optical axis, or may transform a light beam (e.g. a laser beam) into a ring.

The two axicon lenses may be arranged adjacent to each other. The two axicon lenses may be arranged spaced apart from each other.

In various embodiments, each axicon lens may include a conical surface, wherein respective conical surfaces of the two axicon lenses may be arranged facing each other. In this way, a first axicon lens of the two axicon lenses may receive a light and shape the light to generate the annular illumination pattern 112 to be received by a second axicon lens of the two axicon lenses, wherein the second axicon lens may collimate the annular illumination pattern 112.

In various embodiments, at least one of the two axicon lenses may be movable relative to the other of the two axicon lenses. In other words, one of the axicon lenses may be movable or both axicon lenses may be movable relative to each other. In this way, the separation distance between the two axicon lenses may be adjustable or variable. By adjusting the separation distance between the two axicon lenses, the depth of the sample into which the annular illumination pattern 112 illuminates may be adjustable.

In various embodiments, the optical detection device 100 may further include an additional axicon lens for focusing the annular illumination pattern 112 onto the sample 108 to illuminate the portion 110 of the sample 108. By doing so, a cone shell illumination configuration may be provided. The additional axicon lens may also receive the return light 106.

In various embodiments, the shaping optics may include a mask including a non-transmissive portion (or masked portion). The non-transmissive portion may be configured to selectively block a part of the light received by the mask to generate the annular illumination pattern 112. This may mean that part of the light incident on the mask may not pass through the non-transmissive portion, while the remaining part of the light may pass through the remaining portion (transmissive portion) of the mask. The size (or cross-sectional dimension, or diameter) of the non-transmissive portion of the mask may be variable. For example, a ring slider with multiple rings each having different dimensions may be used as part of the mask to control the ring dimensions including the ring radius and the ring thickness so as to adjust the non-transmissive portion of the mask. The mask may also receive the return light 106.

In various embodiments, the optical detection device 100 may further include an imaging lens for focusing the annular illumination pattern 112 onto the sample 108 to illuminate the portion 110 of the sample 108. By doing so, a cone shell illumination configuration may be provided. The imaging lens may also receive the return light 106. For example, the imaging lens may be an objective lens or a microscope objective lens.

In various embodiments, the imaging lens may be arranged adjacent to the mask.

In various embodiments, the optical detection device 100 may further include a collimation lens to collimate the light to be received by the mask. This may mean that the light received by the mask may be collimated (e.g. a collimated light beam).

In one embodiment, the collimation lens, or sometimes referred interchangeably as collimating lens, may be arranged adjacent to the mask. Such an arrangement may form part of a hybrid configuration with a cone shell configuration for illumination. For example, the hybrid configuration may include a cone configuration for detection.

In various embodiments, the optics arrangement 102 may further include a light director arranged to optically couple or direct the light (for example, the collimated light or the annular illumination pattern 112) towards the portion 110 of the sample 108. The light director may further optically couple the return light 106 towards the detector arrangement 104. Further, in various embodiments, the light director may optically divide the light into two separate light portions. For example, the light director may include a beam splitter or a dichroic mirror.

In various embodiments, the shaping optics may include an axicon lens configured to generate the annular illumination pattern 112 and may further be configured to focus the annular illumination pattern 112 onto the sample 108 to illuminate the portion 110 of the sample 108. By doing so, a cone shell illumination configuration may be provided. The axicon lens may also receive the return light 106. The axicon lens may be arranged adjacent to the sample 108. The axicon lens may be arranged between the sample 108 and a light director.

In various embodiments, the optical detection device 100 may further include a collimation lens to collimate the light to be received by the axicon lens. This may mean that the light received by the axicon lens may be collimated (e.g. a collimated light beam).

In various embodiments, the optical detection device 100 may further include a fiber or a fiber assembly arranged to receive the return light 106 and to optically couple the return light 106 to the detector arrangement 104.

In various embodiments, the fiber assembly may include a plurality of fibers arranged in a plurality of concentric patterns at one end of the fiber assembly to receive the return light 106. As examples, each fiber in the plurality of fibers may be a single-mode fiber, or a multi-mode fiber.

In various embodiments, fibers arranged in a respective concentric pattern of the plurality of concentric patterns may be arranged into a linear block at an opposite end of the fiber assembly. This may mean that at the opposite end of the fiber assembly, the plurality of fibers may be arranged into a plurality of linear blocks, where the number of linear blocks may correspond to the number of the concentric patterns. In various embodiments, a respective linear block may correspond to a respective section of a detector in the detector arrangement 104. This may mean that lights from fibers arranged in a respective linear block may be optically coupled to a respective section of a detector in the detector arrangement 104.

In various embodiments, the optical detection device 100 may further include a focusing lens arranged to focus the return light 106 to the fiber or the fiber assembly. For example, the focusing lens may be an objective lens or an imaging lens.

In various embodiments, the detector arrangement 104 may include a spectrometer (or a spectrograph) for spectrally dispersing the return light 106 for detection.

In various embodiments, the detector arrangement 104 may include a detector to detect the return light 106. In the context of various embodiments, the detector may be capable of generating a two-dimensional image or spectral image based on the return light 106. For example, the detector may be a charge-coupled device (CCD).

In various embodiments, the optical detection device 100 may further include a filter for filtering the return light. For example, the filter may be a long pass filter (LPF).

In various embodiments, the optical detection device 100 may further include a light source, wherein the optics arrangement 102 may be configured to generate the annular illumination pattern 112 based on a light produced by the light source. For example, the light source may include a laser.

In various embodiments, the optical detection device 100 may be a portable or a handheld optical detection device.

In the context of various embodiments, the annular illumination pattern 112 may have a ring thickness in a range of about 0.5 mm to about 3.5 mm, or about 1 mm to about 3 mm. For example, the ring thickness may be, but is not limited to, about 1 mm, about 2 mm or about 3 mm.

In the context of various embodiments, the annular illumination pattern 112 may, have a ring radius (e.g. an inner radius of the annular illumination pattern 112) in a range of about 0.1 mm to about 6.5 mm, or about 2 mm to about 6 mm. For example, the ring radius may be, but is not limited to, about 2 mm, about 4 mm or about 6 mm.

In the context of various embodiments, the annular illumination pattern 112 may, for example, be provided to a depth of focal point in the sample 108 (e.g. tissue) in a range of about 0.1 mm to about 1.0 mm, or about 0.3 mm to about 0.5 mm. For example, the depth of focal point may be, but is not limited to, about 0.1 mm, about 0.3 mm, about 0.5 mm or about 1.0 mm.

In the context of various embodiments, the fiber or each fiber of the fiber assembly may, for example, have a fiber diameter in a range of about 0.1 mm to about 0.5 mm, or about 0.1 mm to about 0.4 mm. For example, the fiber diameter may be, but is not limited to, about 0.1 mm, about 0.2 mm, or about 0.4 mm.

In one example, for a depth of focal point (or focus) of about 0.3 mm, the annular illumination pattern 112 may have a ring radius of about 6 mm, and a ring thickness of about 2 mm. The detection fiber size may be about 0.1 mm.

In another example, for a depth of focal point (or focus) of about 1.0 mm, the annular illumination pattern 112 may have a ring radius of about 6 mm, and a ring thickness of about 3 mm. The detection fiber size may be about 0.4 mm.

In various embodiments, the optical detection device 100 may be employed for various measurements, e.g. for diffuse reflectance measurement or for Raman measurement.

In various embodiments, the light source may have a maximum output power of about 30 mW at a wavelength about 405 nm.

Figure 1B:
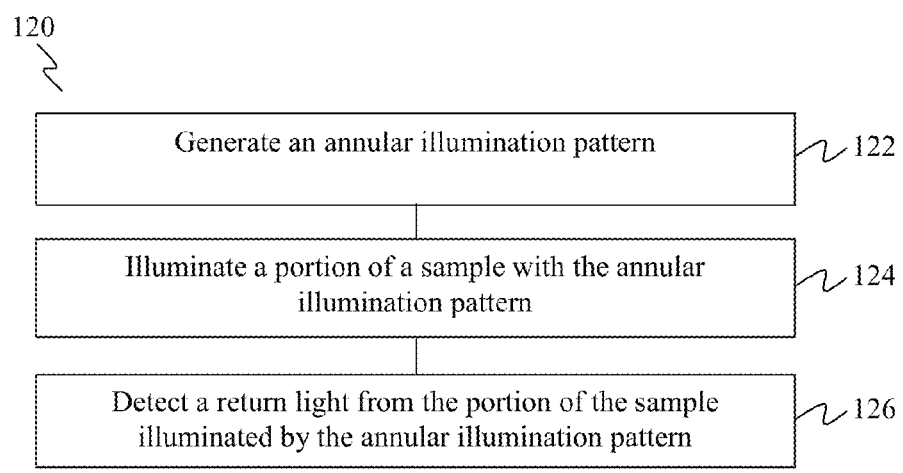
FIG. 1B shows a flow chart illustrating an optical detection method, according to various embodiments.

FIG. 1B shows a flow chart 120 illustrating an optical detection method.

At 122, an annular illumination pattern is generated.

At 124, a portion of a sample is illuminated with the annular illumination pattern.

At 126, a return light is detected from the portion of the sample illuminated by the annular illumination pattern.

In various embodiments, the optical detection method 120 may be performed using the optical detection device 100 (FIG. 1A), according to various embodiments.

In the context of various embodiments, the sample (e.g. 108) may, for example, include a tissue, or a tissue phantom, or a two-layered agar phantom, or a turbid medium.

Various embodiments may provide various apparatus setups for a non-contact, lens-based spectroscopy.

Various embodiments may provide an apparatus setup which may include a cone shell illumination configuration, and a cone shell detection configuration, whereby when in the cone shell illumination configuration, light from a source may be passed through a first axicon lens and a second axicon lens to create a laser ring, where the laser ring may then be focused onto a sample for illumination through a third axicon lens; and when in a cone shell detection configuration, the signals emitted from the illuminated sample may be transmitted through the third axicon lens, and focused onto a collection fiber that may be coupled to a spectrograph equipped with a holographic grating and a charge-coupled device (CCD), where an image may be captured. The image may include the signals emitted from the illuminated sample.

Various embodiments may provide an apparatus setup which may include a cone shell illumination configuration, and a cone shell detection configuration, whereby when in the cone shell illumination configuration, collimated light beam from a source may be passed through a mask with a ring opening to create a laser ring, where the laser ring may then focused onto a sample for illumination through one axicon lens; and when in a cone shell detection configuration, the signals emitted from the illuminated sample may be transmitted through the axicon lens and the ring opening in the mask, and focused onto a collection fiber that may be coupled to a spectrograph equipped with a holographic grating and a CCD, where an image may be captured. The image may include the signals emitted from the illuminated sample.

Various embodiments may provide an apparatus setup which may include a cone shell illumination configuration, and a cone shell detection configuration, whereby when in the cone shell illumination configuration, collimated light beam from a source may be passed through one axicon lens create multiple laser rings, where the laser rings may then be focused onto a sample for illumination, and when in a cone shell detection configuration, the signals emitted from the illuminated sample may be transmitted through the axicon lens, and focused onto a fiber assembly including or consisting of a plurality of rings of collection fibers. Each ring of the collection fibers may be arranged at a different radial distance from the center of the fiber assembly and may collect light corresponding to a particular depth. On the other end of the fiber assembly, the fibers may be rearranged to couple to a spectrograph equipped with a holographic grating and a CCD, where an image may be captured, such that the spectra corresponding to each depth may be collected at the same time. The image may include the signals emitted from the illuminated sample. In various embodiments, a laser cone shell may be generated when a thin collimated annular laser beam passes through an axicon lens. In further embodiments, a laser cone may be generated when a full round collimated laser beam passes through an axicon lens. In such cases, the full round collimated beam may be treated as multiple thin collimated annular laser beams with different diameters; while the laser cone may be treated as multiple laser cone shells stacked together.

Apparatus setups according to various embodiments may be used for optical measurements, not limited to diffuse reflectance or Raman measurements.

Various embodiments may also provide a method of implementing a non-contact, lens-based spectroscopy using the apparatus setups according to various embodiments.

A numerical method, for example a Monte Carlo method, for modelling non-contact diffuse reflectance measurements in a lens based setup with a cone or cone shell configuration will now be described by way of the following non-limiting examples.

In various non-limiting examples, a numerical method may be used to simulate diffuse reflectance measurements from a squamous cell carcinoma (SCC) tissue model in different cone shell, cone and hybrid configurations for optical spectroscopy. The performance of these three configurations in terms of the sensitivity to the tumor and the stroma of the SCC tissue may be compared to each other.

Figure 2A:
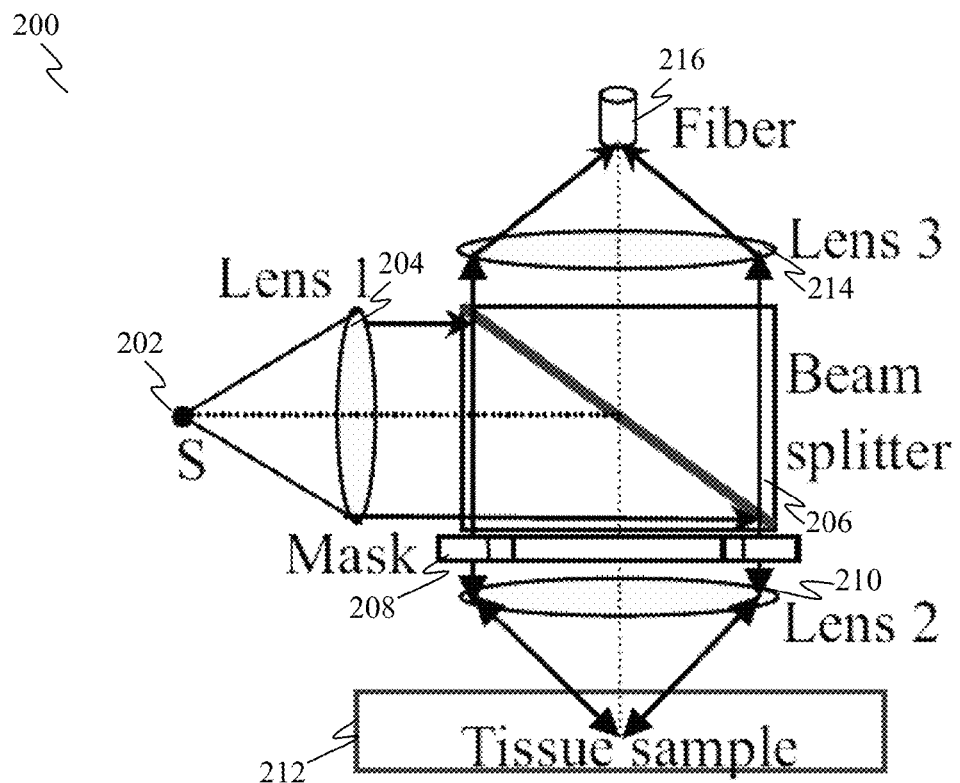
FIG. 2A shows a schematic side view of a lens based set up for non-contact diffuse reflectance measurements, according to various embodiments.

FIG. 2A shows a schematic view of a lens based set up 200 for non-contact diffuse reflectance measurements, according to various embodiments.

In various embodiments, white light from a point source, S 202, may be first collimated by Lens 1 204 into a polarizing cube beam splitter 206, and then focused into a tissue sample 212 via Lens 2 210. For example, Lens 2 210 may also be called an imaging lens in accordance with its role in measurements. Diffusely reflected light from the tissue sample 212 may be collected by Lens 2 210 and collimated into the polarizing cube beam splitter 206, which may then be focused into a detection fiber 216 by Lens 3 214. The detection fiber 216 may deliver the light to a spectrometer (not shown in FIG. 2A). The polarizing cube beam splitter 206 may reflect one component of light with a particular polarization, for example the S component, while allowing the other component of light, for example the P component, to transmit through. The role of the beam splitter 206 in this setup 200 may be to minimize the contribution of specular reflectance. Lens 2 210 and Lens 3 214 may be assumed to possess equal focal distances. A mask 208 may be placed between the beam splitter 206 and Lens 2 210.

Figure 2B:
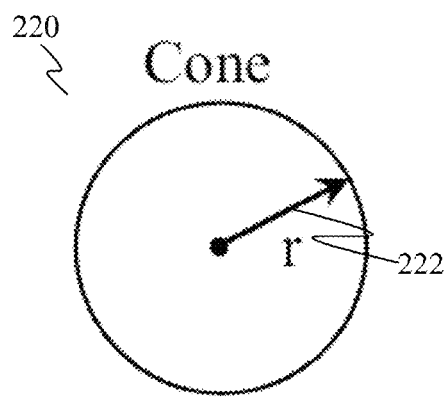
FIG. 2B shows a schematic view of a mask having a shape corresponding to a full circular illumination pattern for a cone illumination configuration.

The shape of the intersection between light and the sample volume in an optically transparent sample may typically be a cone, in which case, light intersecting with the plane of Lens 2 210 forms a circle. In this case, the mask 208 (FIG. 2A) may have a shape or pattern corresponding to a circle 220 as shown in FIG. 2B, so as to provide cone illumination.

Figure 2C:
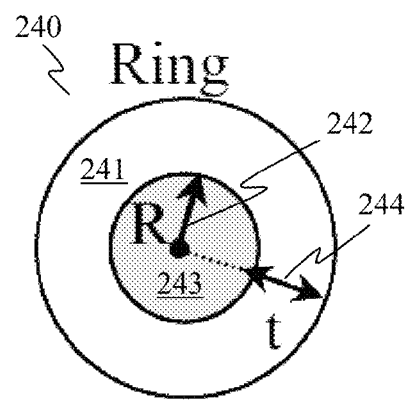
FIG. 2C shows a schematic view of a mask having a shape corresponding to a ring or annular illumination pattern for a cone shell illumination configuration.

In various embodiments, there may be provided a configuration in which the shape of intersection between light and sample volume may be a cone shell, and consequently light intersecting with the plane of Lens 2 210 may form a ring. In this case, the mask 208 (FIG. 2A) may have a shape or pattern corresponding to a ring pattern 240 as shown in FIG. 2C. Light may pass through the ring 241 (annular) area (or peripheral area) but may be blocked in the area (e.g. non-transmissive portion) 243 enclosed by the ring area 241. Therefore, in the cone shell configuration, the mask 208 having the ring pattern 240 may be used to block at least some part of the light received by the mask 208.

The mask 208, placed between the beam splitter 206 and Lens 2 210, may be used to change the dimensions of the cone or cone shell configuration. For example, a diaphragm serving as the mask 208 may be used to control the radius of the circle in the cone configuration, i.e. r 222 (FIG. 2B); while a ring slider with multiple rings each having different dimensions as the mask 208 may be used to control the ring dimensions including the ring radius R 242 (FIG. 2C) and the thickness t 244 (FIG. 2C) in the cone shell configuration.

The cone configuration may be seen as a special case of the cone shell configuration in which the ring radius R 242 is zero.

Both illumination and detection may be affected by the mask 208 in FIG. 2A because it is located right next to the imaging lens, i.e. Lens 2 210.

In various embodiments, if a ring slider is placed between Lens 1 204 and the beam splitter 206 and a diaphragm is placed between Lens 3 214 and the beam splitter 206 at the same time, a hybrid configuration may be provided with a cone shell configuration for illumination and a cone configuration for detection.

The tissue sample 212 may be positioned on a sample stage. The sample stage may be moved up and down to vary the imaging depth (or focal depth). Additionally or alternatively, Lens 2 210 may be adjusted to change the depth of focal point in the tissue sample 212.

In principle, most non-contact setups for diffuse reflectance spectroscopy may be similar to the abovementioned setup in terms of the illumination and detection configuration. In this sense, the methodology and most results obtained may generally be applicable to several other non-contact lens based systems for diffuse reflectance measurements.

In various embodiments, the mask 208 may be a shaping optics or part of a shaping optics. Lens 1 204 may be a collimation lens. Lens 3 214 may be a focusing lens.

Cone shell illumination for Monte Carlo simulation will now be described.

Monte Carlo method for simulating focused light beam, e.g. cone configuration for illumination, may be extended to the cone shell illumination. Subsequently, a numerical method may be used to simulate the cone shell detection.

Only the cone shell configuration will be described here because as previously mentioned, the cone configuration may be treated as a special case of the cone shell configuration in which the ring radius is zero.

Figure 3:
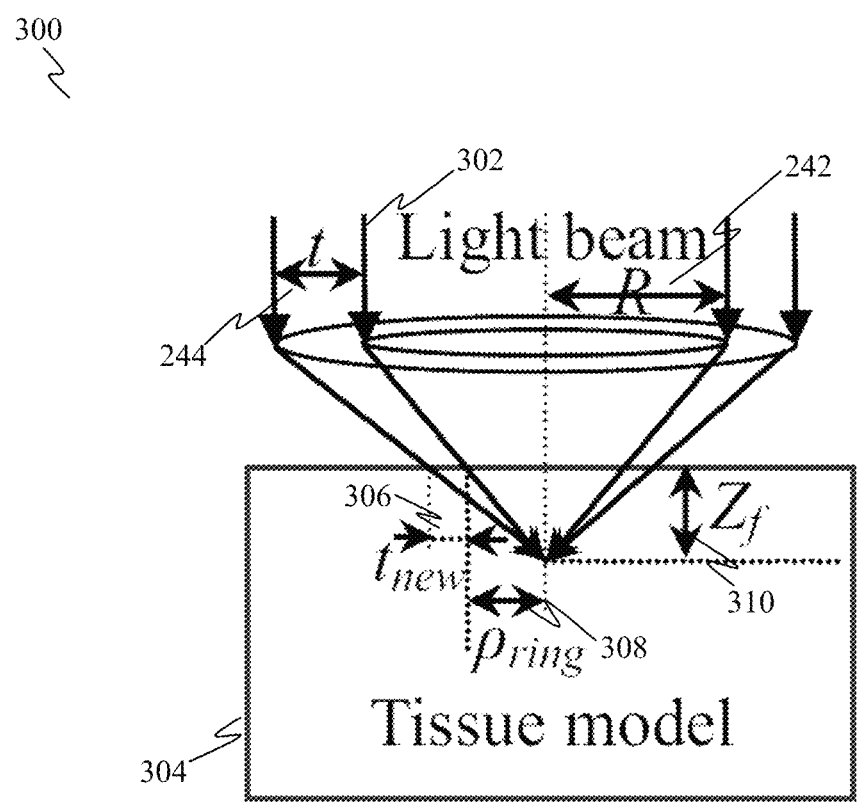
FIG. 3 shows a schematic side view of a cone shell illumination configuration, according to various embodiments.

FIG. 3 shows a schematic side view of a cone shell illumination configuration 300, according to various embodiments.

The ring radius, ring thickness, the imaging lens's focal length and the depth of focal point in the tissue may separately or in combination define a cone shell configuration. The four parameters may be denoted by R 242, t 244, focal depth (f) and the depth of focal point from the incident surface of the sample ($Z_f$) respectively. The maximum value of R 242 may not be larger than the radius of the lens. The lens used may be treated as ideal, and thus the lens thickness need not be taken into account.

A Cartesian coordinate system may be set up in the simulation to facilitate tracking the positions of photons. Referring to FIG. 3, the origin may be the center of the incident light beam 302 on the surface of the tissue model 304. For example, the tissue model may be the tissue sample 212 (FIG. 2A). The Z axis may be the normal of the surface pointing towards the inside of the turbid medium (e.g. the tissue model 304 or part thereof). The x-y plane may be located on the surface of the tissue model 304. The focused light beam 302 may form a ring with a radius of $\rho_{ring}$ 308 and a thickness of $t_{new}$ 306 on the tissue surface as shown in FIG. 3.

The radius and the thickness of the illumination ring on the tissue surface may be calculated from R 242 and t 244 as follows.

$$\frac{\rho_{ring}}{R} = \frac{Z_f}{f}, \quad \text{(Equation 1)}$$

$$\frac{t_{new}}{t} = \frac{Z_f}{f}. \quad \text{(Equation 2)}$$

The irradiance may be assumed to be uniform on the surface of the turbid medium and the radial position of a photon packet may be sampled using the following:

$$\rho = \sqrt{[(\rho_{ring}+t_{new})^2 - \rho_{ring}^2]\epsilon_\rho + \rho_{ring}^2} \quad \text{(Equation 3)},$$

where $\epsilon_\rho$ may be a random number uniformly distributed between 0 and 1.

The azimuthal angle of the photon packet may be sampled using the following:

$$\theta = 2\pi\epsilon_\theta \quad \text{(Equation 4)},$$

where $\epsilon_\theta$ may be a random number uniformly distributed between 0 and 1.

The Cartesian coordinates of the incident point may then be determined using the following:

$$x = \rho \cos(\theta) \quad \text{(Equation 5)},$$

$$y = \rho \sin(\theta) \quad \text{(Equation 6)}.$$

The directional cosines may be set as following:

$$u_x = -x/\sqrt{\rho^2 + Z_f^2} \quad \text{(Equation 7)},$$

$$u_y = -y/\sqrt{\rho^2 + Z_f^2} \quad \text{(Equation 8)},$$

$$u_z = Z_f/\sqrt{\rho^2 + Z_f^2} \quad \text{(Equation 9)}.$$

If the ambient medium and the tissue have the same refractive index, the directional cosines need not be changed when the photon enters the tissue. Otherwise, the directional cosines may be changed based on Snell's law and the specular reflection may be taken into account based on the Fresnel law. Once the photon is launched into the tissue model 304, the treatment of photon tracing may be the same as that carried out in L. H. Wang, S. L. Jacques, and L. Q. Zheng, "Mcml—Monte-Carlo Modeling of Light Transport in Multilayered Tissues", Comput. Meth. Prog. Bio. 47(2), 131-146 (1995), the entire disclosure of which is incorporated herein by reference.

Cone shell detection in Monte Carlo simulation will now be described.

Besides the parameters associated with the lens mentioned above, e.g. R 242, t 244, f (for example, f 412 of FIG. 4A) and $Z_f$ 310 (FIG. 3), two additional parameters associated with the detection fiber 216 (FIG. 2A), including the fiber diameter and the numerical aperture (NA), may also be used to define the cone shell detection.

Figure 4A:
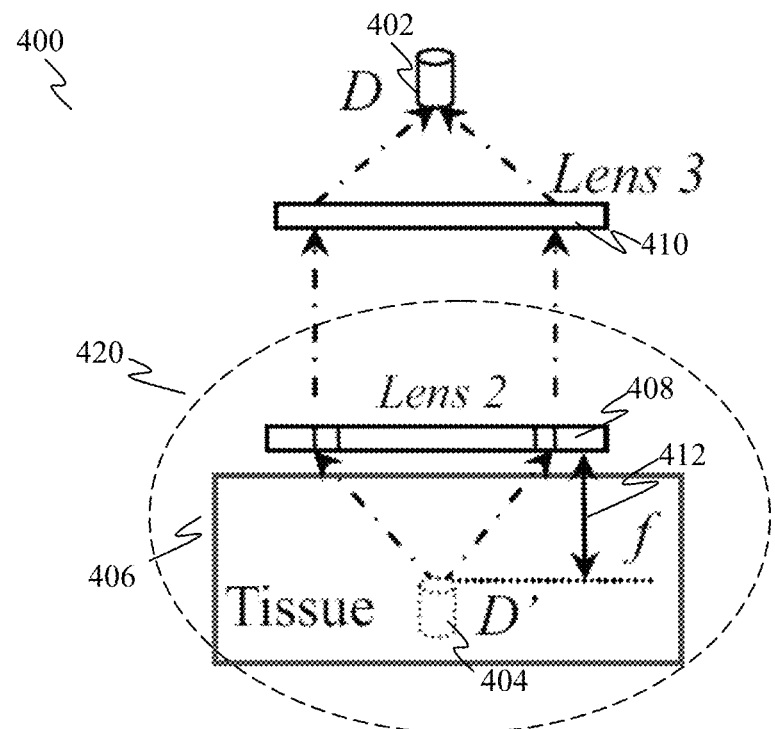
FIG. 4A shows a schematic diagram illustrating the evaluation of the cone shell detection, according to various embodiments.

The detection part of the setup may be simplified as shown in FIG. 4A.

For simplication purposes, the thickness of the mask (for example, the mask 208 of FIG. 2A) may be assumed to be zero. Since both the imaging lens (for example, Lens 2 210 of FIG. 2A) and the mask may be treated as infinitely thin, the two components may be merged into Lens 2 408 as shown in FIG. 4A, which shows a schematic diagram illustrating cone shell detection. The detection fiber D 302 may be placed at the focal plane of Lens 3 410. An image of the fiber D 302 may be formed in the tissue model 406 on the focal plane of Lens 2 408, which is denoted as D' 404 in FIG. 4A. As Lens 2 408 and Lens 3 410 may possess equal focal distances, D 402 and D' 404 may have an equal size. Due to the reciprocity of ray tracing, finding whether a photon is detected by fiber D 402 may be equivalent to identifying whether the photon may be traced back to its image D' 404 and the latter scenario may be easier to solve.

Figure 4B:
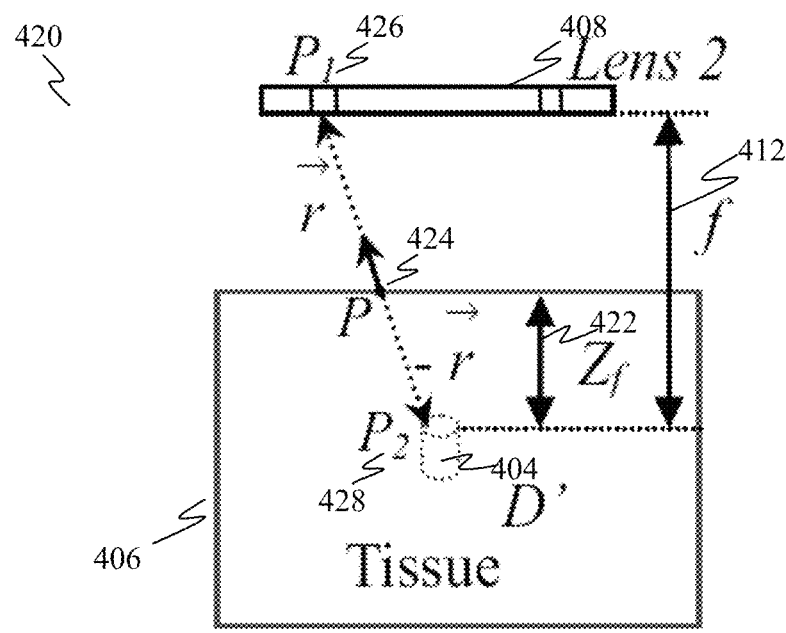
FIG. 4B shows an expanded view of an encircled area 420 of FIG. 4A.

FIG. 4B shows a detailed view of the cone shell detection at the interface of Lens 2 408 and the tissue model 406, illustrating how an exiting photon may be traced back to D' 404. Once a photon exits the tissue surface in a direction of $\vec{r}$ from position P 242, two steps may be performed to determine whether this photon may be detected by the detector.

The first step may determine whether this photon passes through the ring. This may be done by moving the photon from P 424 to the plane of Lens 2 408 along $\vec{r}$ and finding the intersection with the plane of Lens 2 408, which may be denoted by $P_1$ 426. If $P_1$ 426 is located within the ring, it may suggest that the photon passes through the ring, then the photon may continue to go through the second step, otherwise the detection procedure for this photon may be terminated.

The second step may perform ray retracing to determine whether this photon may be detected by the detection fiber. This may be done by moving the photon from P 424 along vector $-\vec{r}$ towards the plane of $Z = Z_f$ 422 and checking whether the intersection with the plane, as denoted by $P_2$ 428, may be located within the fiber tip area. If affirmative, the exiting angle of this photon may be compared to the acceptance angle of the fiber, which may be calculated from the NA value. If the exiting angle is also smaller than the fiber acceptance angle, the photon may be counted as being detected by the fiber; otherwise the photon may be rejected. If a photon is detected by the fiber, all related trajectory information may be recorded. It may be assumed that the mismatch of refractive indices of the tissue model 406 and the ambient medium above the tissue 406 may not affect the ray retracing step. This may be due to the fact that D' 404 is an image of D 402. In the retracing procedure, the virtual medium around D' 404, which is the "image" of the medium around D 402, may have the same refractive index as that of the medium around D 402, which may happen to be equal to the refractive index of the ambient medium above the tissue 406.

Validation of the Monte Carlo method will now be described.

To validate the Monte Carlo method, several simulations may be performed.

The illumination scheme described above may be validated against published results, and agreement therebetween may be established.

To validate the detection scheme, another set of simulations in a semi-infinite homogeneous tissue model may be performed. The optical properties of the tissue model may include the tissue refractive index $n_t = 1.4$, the absorption coefficient $\mu_a = 1.0$ cm$^{-1}$, the scattering coefficient $\mu_s = 100$ cm$^{-1}$, and the anisotropy g=0.9. The refractive index of the ambient medium may also be set to about 1.4 such that there may be no refractive index mismatch on the top surface of the tissue model (for example, the tissue 406 of FIG. 4B). The diameter of the detection fiber 402 may be about 2 mm and the NA may be set to about 0.6. The radii of Lens 2 408 and Lens 3 410 may be about 10 mm while the focal lengths may be set to about 20 mm. Both the ring radius and the ring thickness may be set to about 5 mm. The depth of focal point of the imaging lens, i.e. Lens 2 408, in the tissue model 406 may be varied from about 0.5 mm to about 1.0 mm at an increment of about 0.5 mm.

Figure 5A:
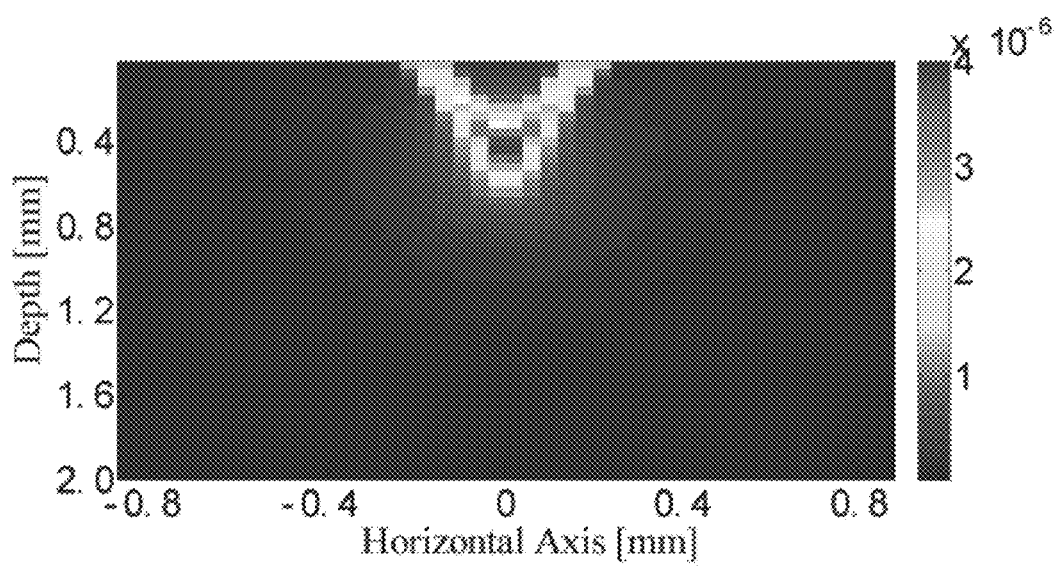
FIG. 5A shows a plot of absorption distribution of detected photons in a simulation with the depth of focal point in a tissue being 0.5 mm.
Figure 5B:
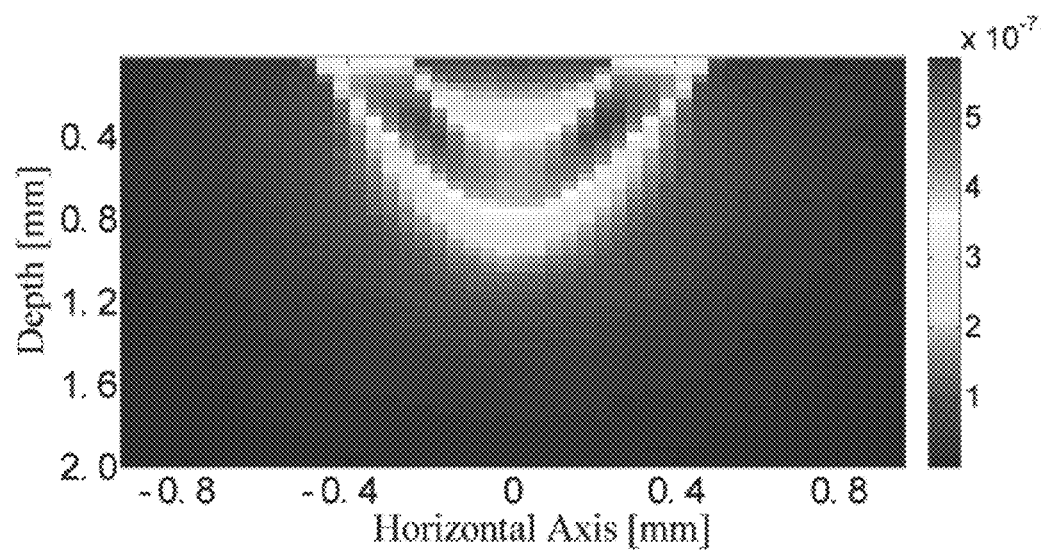
FIG. 5B shows a plot of absorption distribution of detected photons in a simulation with the depth of focal point in a tissue being 1.0 mm.

In each simulation, about 200 million photons may be launched and the grid sizes may be about 0.04 mm in x, y, and z dimensions. The absorption distribution contributed only by detected photons may be as shown in FIGS. 5A and 5B. FIG. 5A shows the result for a first simulation in which the depth of focal point in tissue is about 0.5 mm. Based on the setting described above, the light beam focused onto the turbid medium surface may form a ring with a radius of about 0.125 mm and a ring thickness of about 0.125 mm. FIG. 5A shows that the shape and size of light beam focused onto the medium surface may approximately agree with the predictions that a light beam focused onto the turbid medium surfaces should form a ring with a radius of about 0.125 mm and a ring thickness of about 0.125 mm, in which the blurred boundary of the cone shell may be due to the turbidity of the tissue model. The brightest spot in the tissue model 406 may be located at a depth of around 0.5 mm, which agrees with the depth of the focal point in the tissue model 406 set in the simulation parameters. The result for another situation, e.g. when the depth of the focal point in the tissue model is about 1.0 mm, is shown in FIG. 5B.

Based on the setting for the exemplary situation when the depth of the focal point in the tissue model is about 1.0 mm, the light beam focused onto the turbid medium surface may form a ring with a radius of about 0.25 mm and a ring thickness of about 0.25 mm. FIG. 5B shows that the shape and size of light beam focused onto the medium surface may approximately agree with the predictions that a light beam focused onto the turbid medium surface should form a ring with a radius of about 0.25 mm and a ring thickness of about 0.25 mm. It may be observed that there may be no single obvious focus in the absorption distribution and the distribution may shift towards the superficial area. Moreover, the bottom edge of the absorption distribution may be located around 0.8 mm, which may likely be due to the joint effects of tissue turbidity and the cone shell detection scheme. Based on the results shown in FIGS. 5A and 5B, it may be seen that the Monte Carlo method for the cone shell configuration of illumination and detection may be validated.

Depth sensitive diffuse reflectance measurements in epithelial cancer model will now be described, by first looking at an early squamous cell carcinoma model.

Figure 6:
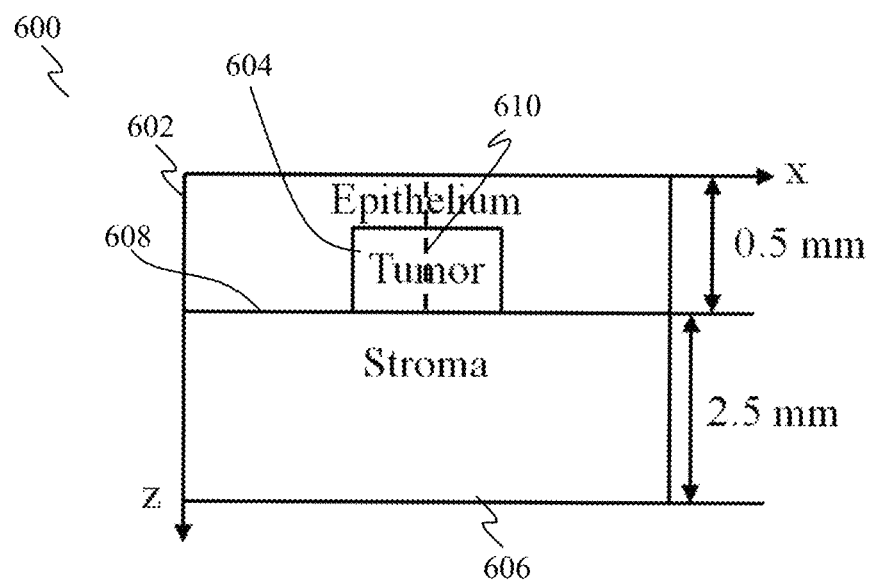
FIG. 6 shows a schematic cross-sectional side view of a squamous cell carcinoma tissue model, according to various embodiments.

An epithelial tissue may typically include or consist of two layers, the top epithelium and the bottom stroma. A model 600 representing a tumor 604 in an early stage is shown in FIG. 6. A basement membrane 608 of the epithelium 602 may separate the two layers, i.e, the epithelium 602 and the stroma 606. The squamous cell carcinoma (SCC) or tumor 604 may usually originate from the basement membrane 608 of the epithelium 602. A simplified early squamous cell carcinoma model may be utilized. In this simplified model, the SCC tumor 604 may be assumed to be a cuboid target whose dimensions and position may be specified. The actual dimensions and position of an SCC tumor 604 in an epithelial tissue may be varied considerably among stages during tumor development. For example, the epithelial thickness may be set to about 0.5 mm. The stromal thickness may be set to about 2.5 mm to represent a semi-infinite layer. The tumor width and length may be both set to about 0.5 mm and the tumor thickness may be set to about 0.3 mm. This SCC model 600 may represent a tumor model in an early stage.

The optical properties of each region may be as listed in Table 1 for a wavelength of about 420 nm. This wavelength may be chosen because it is close to the absorption peak of hemoglobin, which may be the major absorber in human tissues. A refractive index of about 1.4 may be used in all tissue regions. The anisotropy factors of the epithelium 602 and the tumor 604 may be set to about 0.97 and an anisotropy factor of about 0.8 may be used for the stroma 606.

TABLE 1

Optical properties of the SCC tissue model at 420 nm

| Tissue | Optical properties | | |
|---|---|---|---|
|  | $\mu_a(cm^{-1})$ | $\mu_s(cm^{-1})$ | g |
| Epithelium | 3.0 | 42.4 | 0.97 |
| Tumor | 3.0 | 127.2 | 0.97 |
| Stroma | 9.09 | 266.3 | 0.8 |

Note:
$\mu_a$: absorption coefficient; $\mu_s$: scattering coefficient; g: anisotropy Criteria for the evaluation of depth sensitivity in a non-contact setup will now be described. To characterize the depth sensitivity of the non-contact set up, two criteria may be used. The first criterion may be the weighted fraction of photon-scatterer collisions for detected photons, which may mainly be determined by the scattering properties of the tissue model, spent in each region. The numbers of photon-scatterer collisions in the epithelium 602, the SCC 604 and the stroma 606 may be recorded separately for each detected photon, and then the weighted average number of collisions in the each region may be calculated as follows:

$$\overline{NC} = \frac{\sum_{i=1}^{N} W_i * NC_i}{\sum_{i=1}^{N} W_i}, \quad \text{(Equation 10)}$$

where $W_i$ is the exit weight of each detected photon, $NC_i$ is the number of collision spent in the region and N is the total number of detected photons.

The fraction of collisions spent in the tumor (FCT) may be obtained according to the following equation:

$$FCT = \frac{\overline{NC_{tumor}}}{\overline{NC_{epithelium}} + \overline{NC_{tumor}} + \overline{NC_{Stroma}}}. \quad \text{(Equation 11)}$$

The fraction of collisions spent in the epithelium 602 (FCE) and the stroma 606 (FCS) may be obtained similarly.

The second criterion may be the weighted fraction of path length spent in each region for the detected photons. The path length of each detected photon spent in the epithelium 602, the SCC 604 and the stroma 606 may be recorded, and then the weighted average photon path length in each region for all detected photons may be calculated as follows:

$$\overline{PL} = \frac{\sum_{i=1}^{N} W_i * PL_i}{\sum_{i=1}^{N} W_i}, \quad \text{(Equation 12)}$$

where $W_i$ is the exit weight of each detected photon, $PL_i$ is the path length spent in the region and N is the total number of detected photons.

The fraction of path length spent in the tumor (FPLT) may be obtained by:

$$FPLT = \frac{\overline{PL_{tumor}}}{\overline{PL_{epithelium}} + \overline{PL_{tumor}} + \overline{PL_{Stroma}}}. \quad \text{(Equation 13)}$$

The fraction of path length spent in epithelial 602 (FPLE) and in the stroma 606 (FPLS) may be obtained similarly.

Simulation parameters for the cone shell, the cone, and the hybrid configurations will now be described.

To investigate the depth sensitivity of each configuration in diffuse reflectance measurements, a series of simulations may be performed on the SCC model 600. In all simulations, the refractive index of the ambient medium may be set to about 1.0 to represent the refractive index of air, both the radius and the focal length of the imaging lens may be set to about 10 mm, and thus the half angle of light cone formed by the lens may be about 45 degrees for the incident light, and the NA value of the detection fiber may be set to about 1.0 to increase the efficiency of photon detection without losing generality.

The central line of the Lens 2 and Lens 3 (FIG. 2A) may overlap with the middle line of the tumor (dashed line 610 shown in FIG. 6). The parameters investigated in the simulations for the cone shell configuration, the cone configuration and the hybrid configuration involving the cone shell illumination and cone detection, may be listed in Tables 2, 3 and 4 respectively. The cone radius for detection in the hybrid configuration may be equal to the radius of the lens, e.g. about 10 mm. In each independent simulation, about 10 million photons may be used, which may be repeated five times to estimate the means and standard deviations for the construction of error bars (reference made to the results described further below).

TABLE 2

Simulations for the cone shell configuration

| Parameters | Values under investigation |
| --- | --- |
| Ring radius (mm) | 0, 2, 4, 6 |
| Ring thickness (mm) | 1, 2, 3 |
| Depth of focal point in tissue (mm) | 0.1, 0.3, 0.5, 1.0 |
| Detection fiber diameter (mm) | 0.1, 0.2, 0.4 |

TABLE 3

Simulations for the cone configuration

| Parameters | Values under investigation |
| --- | --- |
| Cone radius (mm) | 2, 4, 6, 8 |
| Depth of focal point in tissue (mm) | 0.1, 0.3, 0.5, 1.0 |
| Detection fiber diameter (mm) | 0.1, 0.2, 0.4 |

TABLE 4

Simulations for the hybrid configuration*

| Parameters | Values under investigation |
| --- | --- |
| Ring radius (mm) | 0, 2, 4, 6 |
| Ring thickness (mm) | 1, 2, 3 |
| Depth of focal point in tissue (mm) | 0.1, 0.3, 0.5, 1.0 |
| Detection fiber diameter (mm) | 0.1, 0.2, 0.4 |

*Note:
The cone radius for detection in the hybrid configuration may be equal to the radius of the lens, e.g. about 10 mm.

The results of diffuse reflectance intensity and depth sensitivity in the cone shell configuration will now be described.

Figure 7:
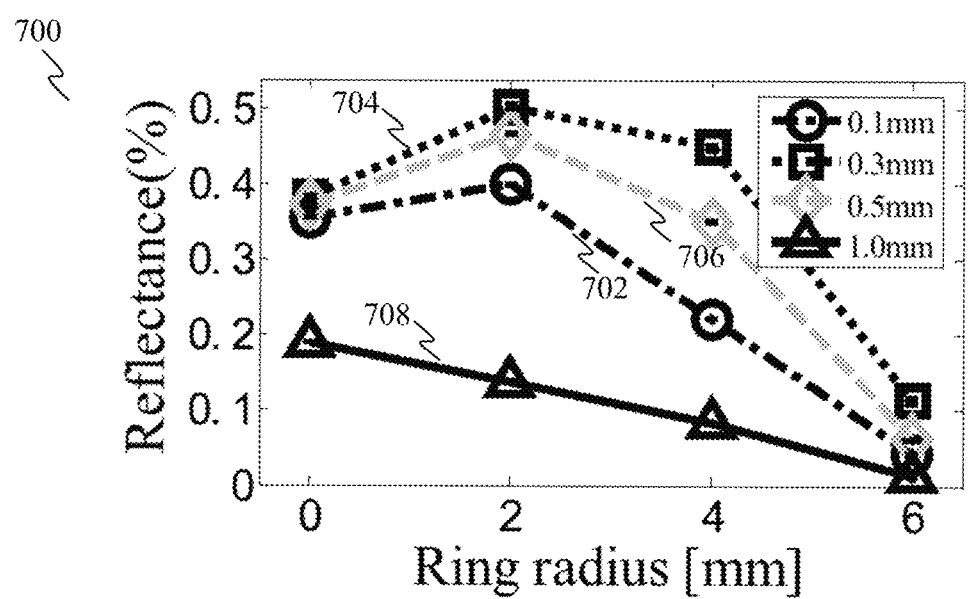
FIG. 7 shows a plot illustrating diffuse reflectance as a function of the ring radius for a range of depths of the focal point in the tissue model in a cone shell configuration, according to various embodiments.

FIG. 7 shows a plot 700 illustrating the simulated diffuse reflectance intensity from the SCC tissue model as a function of the ring radius for the cone shell configuration. Different depths of the focal point in the tissue model in the cone shell configuration may be used. As shown in FIG. 7, each line represents the results for a different depth value as indicated in the legends. The ring thickness and the diameter of the detection fiber may be fixed at about 2 mm and about 0.2 mm, respectively. In FIG. 7, plot line 702 represents the depth of focal point being about 0.1 mm, plot line 704 represents the depth of focal point being about 0.3 mm, plot line 706 represents the depth of focal point being about 0.5 mm, and plot line 708 represents the depth of focal point being about 1.0 mm. The error bars associated with most data points in FIG. 7 may be too small to be observed.

An overall decreasing trend in diffuse reflectance with increasing ring radii may be observed. This may be expected because an increasing ring radius may result in a longer photon path, thus the detected photons may experience larger attenuation. A depth of about 0.3 mm for the focal point in the tissue model may produce the highest diffuse reflectance intensity in all cases. In contrast, a depth of about 1 mm may produce the lowest diffuse reflectance intensity.

Figure 8A:
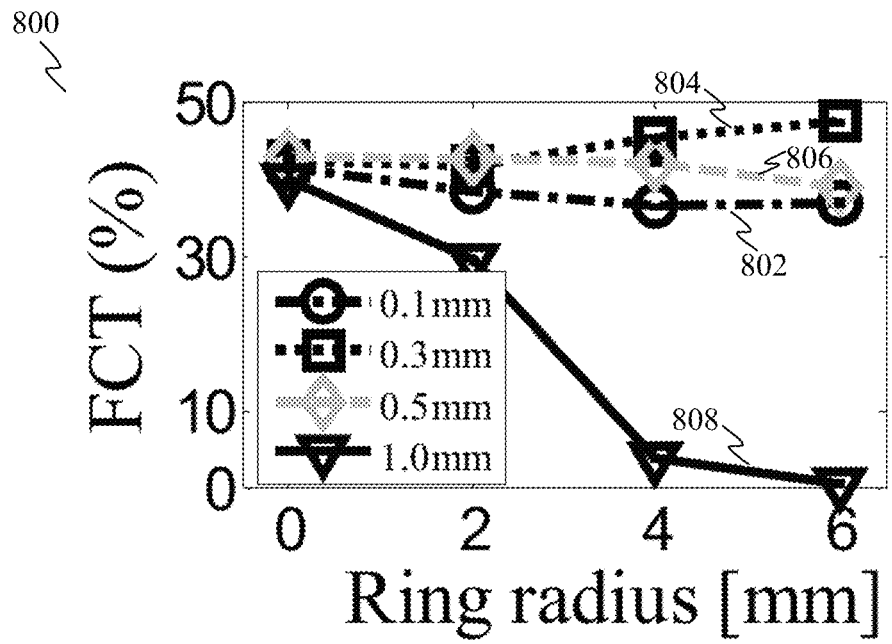
FIG. 8A shows a plot illustrating fraction of collisions in the tumor of the tissue model of FIG. 6 in a cone shell configuration, according to various embodiments.
Figure 8B:
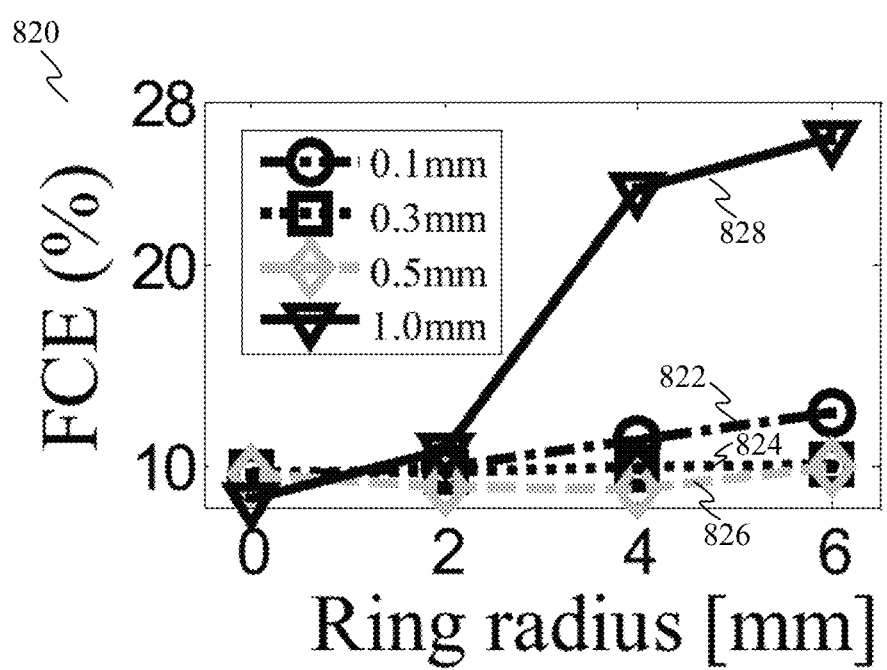
FIG. 8B shows a plot illustrating fraction of collisions in the epithelium of the tissue model of FIG. 6 in a cone shell configuration, according to various embodiments.
Figure 8C:
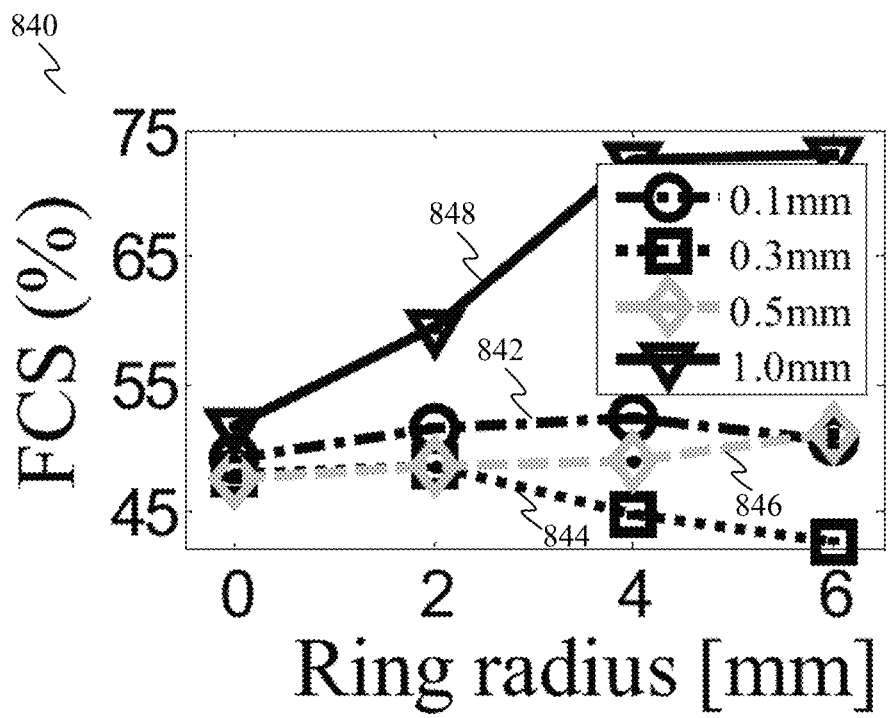
FIG. 8C shows a plot illustrating fraction of collisions in the stroma layer of the tissue model of FIG. 6 in a cone shell configuration, according to various embodiments.

FIGS. 8A to 8C show respective plots illustrating the fraction of collisions spent in the tumor 800, the epithelium 820 and the stroma 840 for the cone shell configuration. As shown in FIGS. 8A to 8C, each line represents the results for a different depth value as indicated in the legends. The ring thickness and the diameter of detection fiber may be fixed at about 2 mm and about 0.2 mm, respectively. In FIG. 8A, plot line 802 represents the depth of focal point being about 0.1 mm, plot line 804 represents the depth of focal point being about 0.3 mm, plot line 806 represents the depth of focal point being about 0.5 mm, and plot line 808 represents the depth of focal point being about 1.0 mm. In FIG. 8B, plot line 822 represents the depth of focal point being about 0.1 mm, plot line 824 represents the depth of focal point being about 0.3 mm, plot line 826 represents the depth of focal point being about 0.5 mm, and plot line 828 represents the depth of focal point being about 1.0 mm. In FIG. 8C, plot line 842 represents the depth of focal point being about 0.1 mm, plot line 844 represents the depth of focal point being about 0.3 mm, plot line 846 represents the depth of focal point being about 0.5 mm, and plot line 848 represents the depth of focal point being about 1.0 mm.

FIG. 8A may suggest that the fraction of collisions in the tumor may not change considerably when the depth of focal point in the tissue model is varied from about 0.1 mm to about 0.5 mm; however it may drop significantly when the depth value is increased to about 1.0 mm. A depth value of about 0.3 mm with a large ring radius, e.g. about 6 mm in FIG. 8A, may yield the most significant contribution from the tumor. FIG. 8C shows that the fraction of collisions in the stroma increases significantly when the ring radius is increased for the depth of about 1.0 mm. The largest ring radius at about 6 mm may produce the highest collision fraction, e.g. around 73%, from the stroma. The fraction of collisions in the epithelium may be significantly affected by the finite width of the tumor. When a small ring radius close to zero is used, the SCC model may be treated as three layers including the thin epithelium, for which a smaller focus depth may produce higher collision fraction in the epithelium. When a larger ring radius is used, the trajectory of most detected photons may get around the tumor. In this case, the SCC model may be treated as two layers including the thick epithelium and the stroma only thus the trend may become quite different.

Figure 9A:
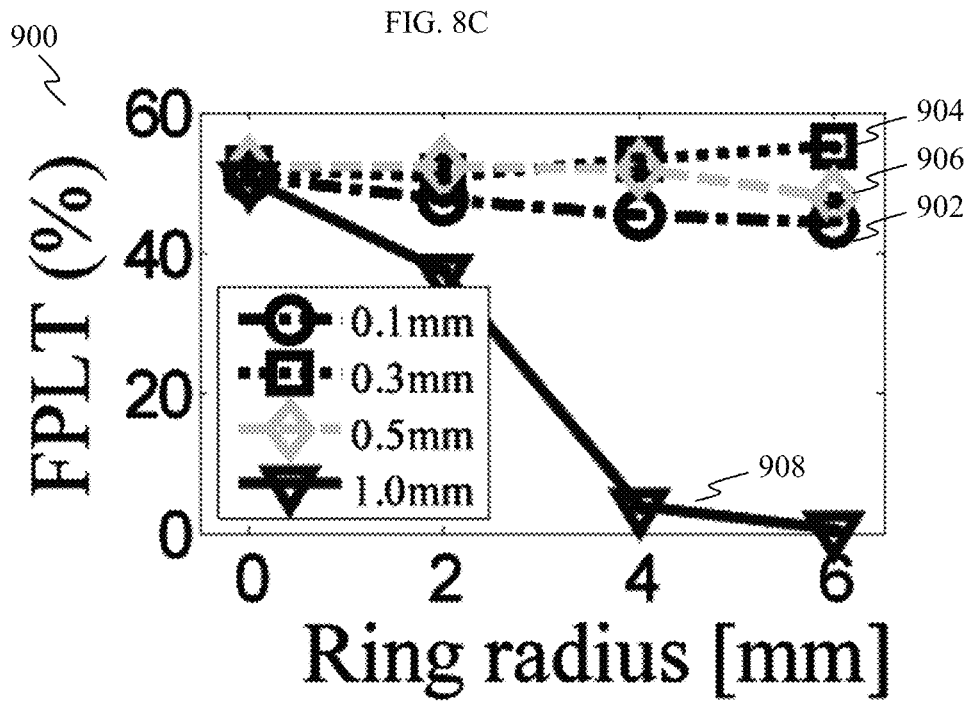
FIG. 9A shows a plot illustrating fraction of path length in the tumor of the tissue model of FIG. 6 in a cone shell configuration, according to various embodiments.
Figure 9B:
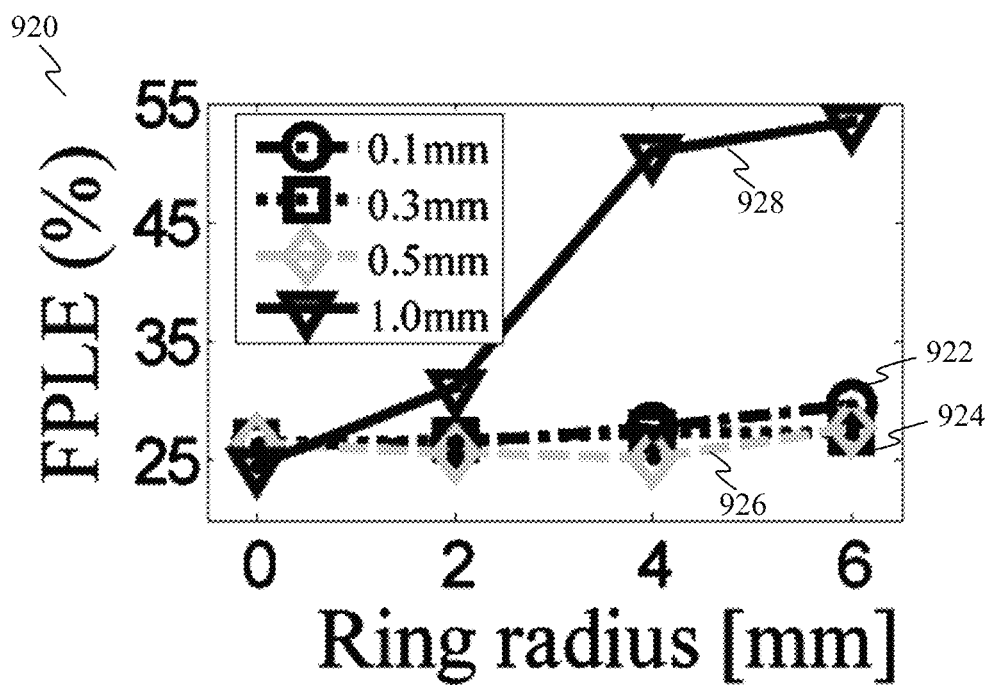
FIG. 9B shows a plot illustrating fraction of path length in the epithelium of the tissue model of FIG. 6 in a cone shell configuration, according to various embodiments.
Figure 9C:
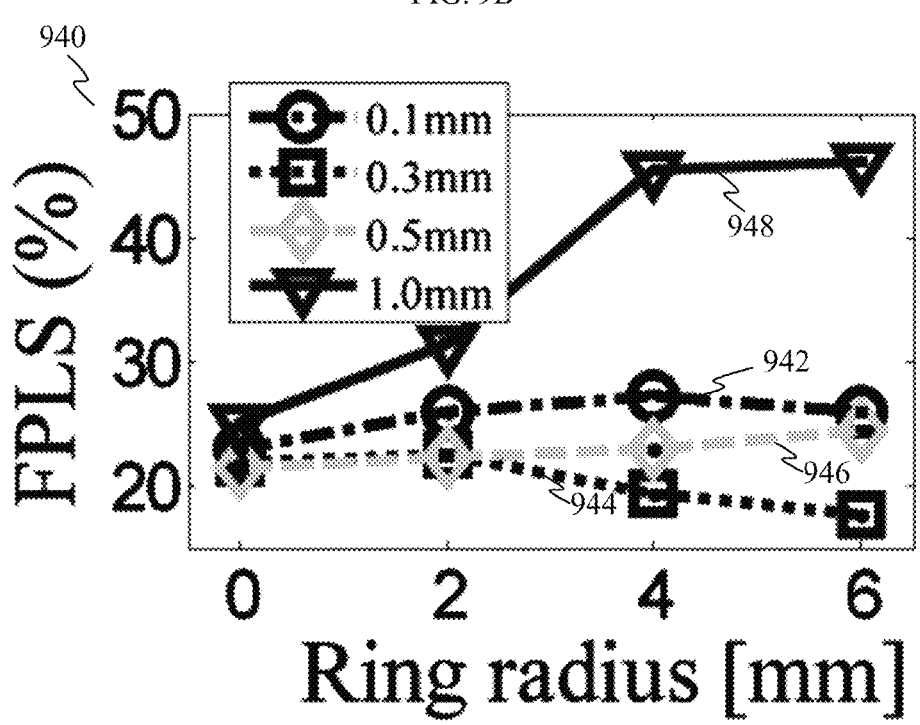
FIG. 9C shows a plot illustrating fraction of path length in the stroma layer of the tissue model of FIG. 6 in a cone shell configuration, according to various embodiments.

FIGS. 9A to 9C show respective plots illustrating the fractions of the path length spent in the tumor 900, epithelium 920 and stroma 940 in the cone shell configuration. As shown in FIGS. 9A to 9C, each line represents the results for a different depth value as indicated in the legends. The ring thickness and the diameter of detection fiber may be fixed at about 2 mm and about 0.2 mm, respectively.

In FIG. 9A, plot line 902 represents the depth of focal point being about 0.1 mm, plot line 904 represents the depth of focal point being about 0.3 mm, plot line 906 represents the depth of focal point being about 0.5 mm, and plot line 908 represents the depth of focal point being about 1.0 mm. In FIG. 9B, plot line 922 represents the depth of focal point being about 0.1 mm, plot line 924 represents the depth of focal point being about 0.3 mm, plot line 926 represents the depth of focal point being about 0.5 mm, and plot line 928 represents the depth of focal point being about 1.0 mm. In FIG. 9C, plot line 942 represents the depth of focal point being about 0.1 mm, plot line 944 represents the depth of focal point being about 0.3 mm, plot line 946 represents the depth of focal point being about 0.5 mm, and plot line 948 represents the depth of focal point being about 1.0 mm.

It may be observed that the trends in FIGS. 9A to 9C may agree with those shown in FIGS. 8A to 8C. Therefore, only the fraction of collisions spent in each region will be shown later below to represent the depth sensitivity of the non-contact setup.

The results on the effect of the ring thickness on the depth sensitivity of the cone shell configuration will now be described.

As the depths of focal point of about 0.3 mm and about 1.0 mm may yield the best sensitivity for the tumor and stroma respectively, only the FCT for a depth of about 0.3 mm and the FCS for a depth of about 1.0 mm are shown below. The effects of ring thickness on the depth sensitivity for cone shell configuration are shown in FIGS. 10A and 10B based on the fraction of collision in the tumor (plot 1000) and the fraction of collision in the stroma (plot 1020), respectively.

Figure 10A:
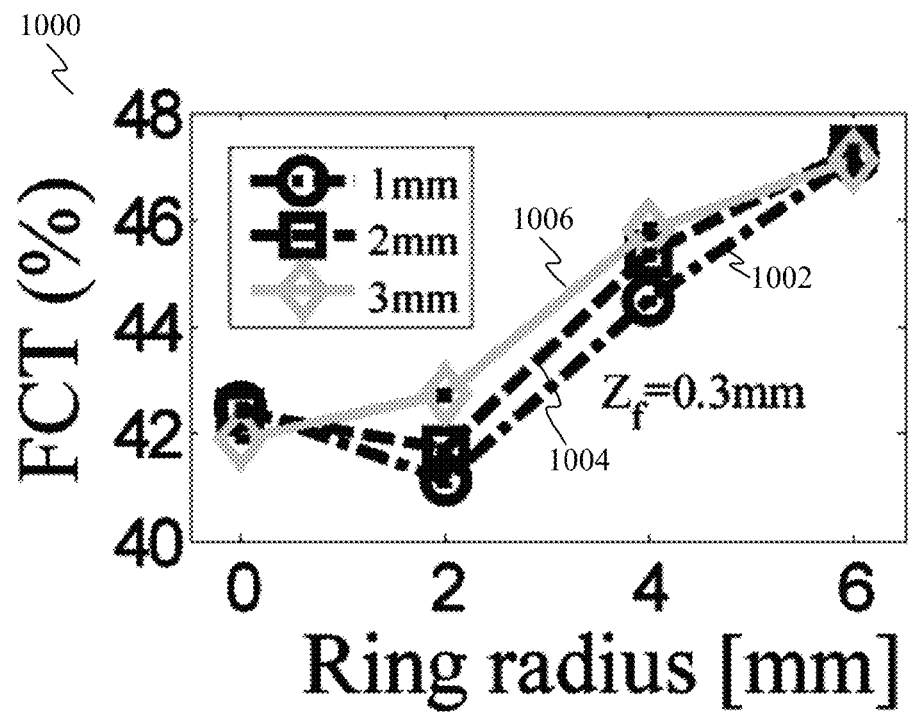
FIG. 10A shows a plot illustrating fraction of collisions in the tumor of the tissue model of FIG. 6 in a cone shell configuration (based on ring thickness), according to various embodiments.
Figure 10B:
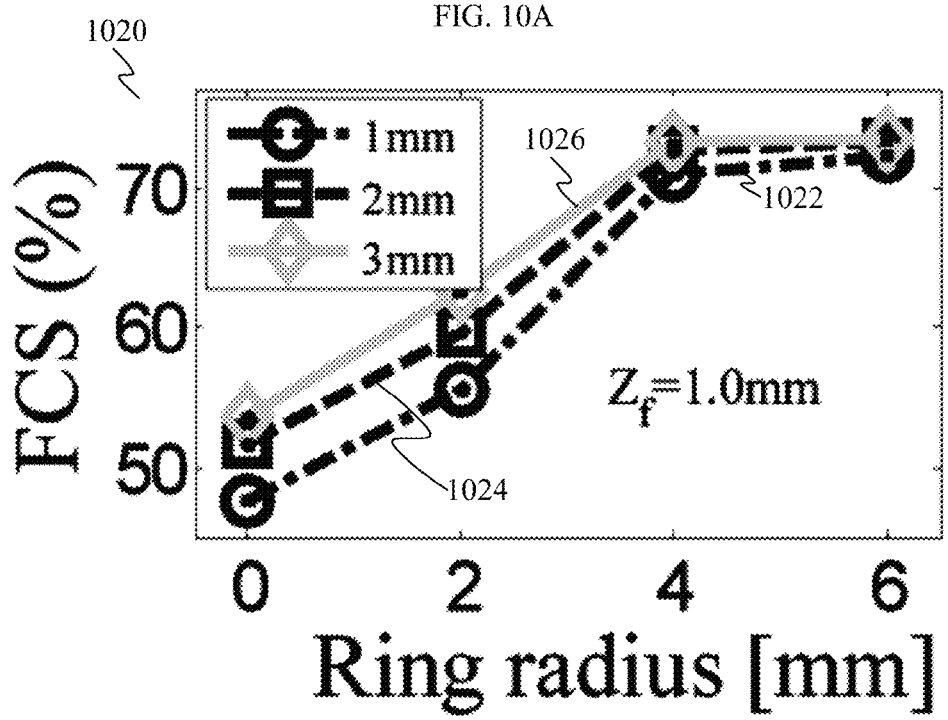
FIG. 10B shows a plot illustrating fraction of collisions in the stroma layer of the tissue model of FIG. 6 in a cone shell configuration (based on ring thickness), according to various embodiments.

As shown in FIGS. 10A and 10B, each line represents the results for a different ring thickness as indicated in the legends. The diameter of detection fiber may be fixed at about 0.2 mm. In FIG. 10A, plot line 1002 represents the ring thickness being about 1 mm, plot line 1004 represents the ring thickness being about 2 mm, and plot line 1006 represents the ring thickness being about 3 mm. In FIG. 10B, plot line 1022 represents the ring thickness being about 1 mm, plot line 1024 represents the ring thickness being about 2 mm, and plot line 1026 represents the ring thickness being about 3 mm.

In FIG. 10A, the depth of focal point in the tissue model, e.g. $Z_f$, is about 0.3 mm; while in FIG. 10B, the depth of focal point in the tissue model, e.g. $Z_f$, is about 1.0 mm. It may be observed that the FCT and FCS may not change significantly when the ring thickness varies.

The results on the effect of the detection fiber size on the depth sensitivity of the cone shell configuration will now be described.

Figure 11A:
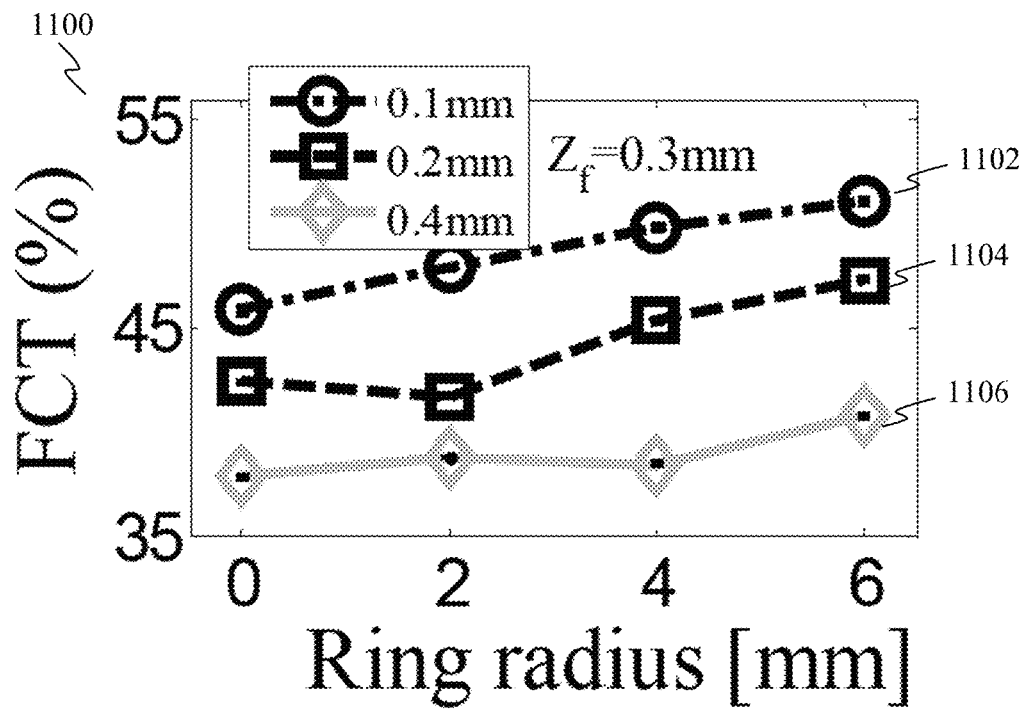
FIG. 11A shows a plot illustrating fraction of collisions in the tumor of the tissue model of FIG. 6 in a cone shell configuration (based on detection fiber size), according to various embodiments.
Figure 11B:
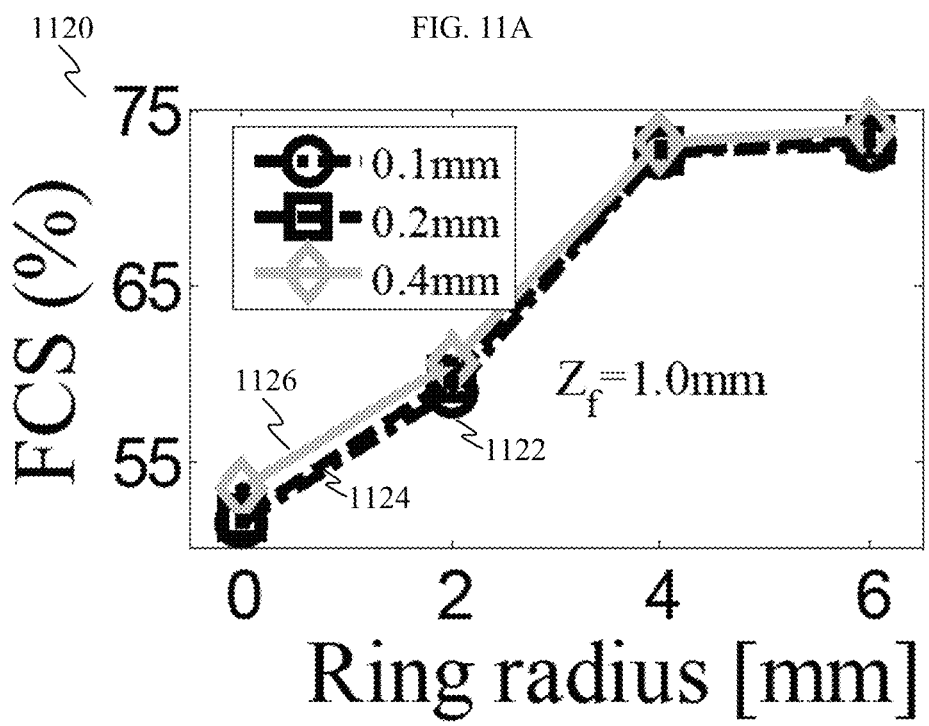
FIG. 11B shows a plot illustrating fraction of collisions in the stroma layer of the tissue model of FIG. 6 in a cone shell configuration (based on detection fiber size), according to various embodiments.

The effects of the detection fiber size on the depth sensitivity of the cone shell configuration are shown in FIGS. 11A and 11B based on the fraction of collision in the tumor (plot 1100) and the fraction of collision in the stroma (plot 1120), respectively. As shown in FIGS. 11A and 11B, each line represents the results for a different detection fiber size as indicated in the legends. The ring thickness may be fixed at about 2 mm. In FIG. 11A, plot line 1102 represents the detection fiber size being about 0.1 mm, plot line 1104 represents the detection fiber size being about 0.2 mm, and plot line 1106 represents the detection fiber size being about 0.4 mm. In FIG. 11B, plot line 1122 represents the detection fiber size being about 0.1 mm, plot line 1124 represents the detection fiber size being about 0.2 mm, and plot line 1126 represents the detection fiber size being about 0.4 mm.

In FIG. 11A, the depth of focal point in the tissue model, e.g. $Z_f$, is about 0.3 mm; while in FIG. 11B, the depth of focal point in the tissue model, e.g. $Z_f$, is about 1.0 mm.

It may be observed from FIG. 11A that, a smaller detection fiber size may provide a higher fraction of collision in the tumor. In FIG. 11B, an opposite trend may be observed but the changes in the fractions in the stroma may be insignificant.

Depth sensitivity in the cone configuration will now be described.

Figure 12A:
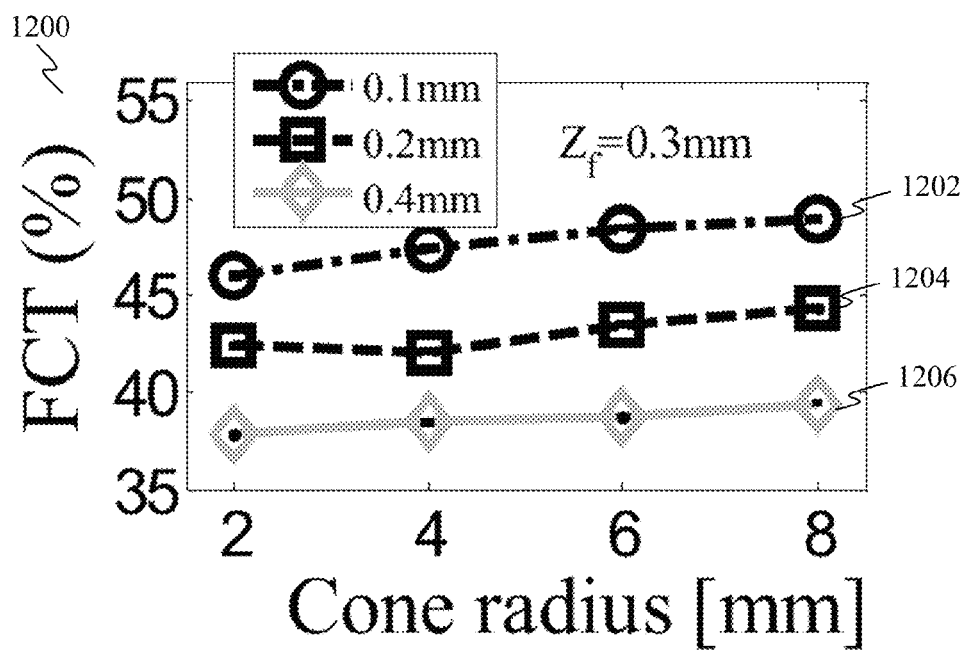
FIG. 12A shows a plot illustrating fraction of collisions in the tumor of the tissue model of FIG. 6 in a cone configuration (based on detection fiber size).
Figure 12B:
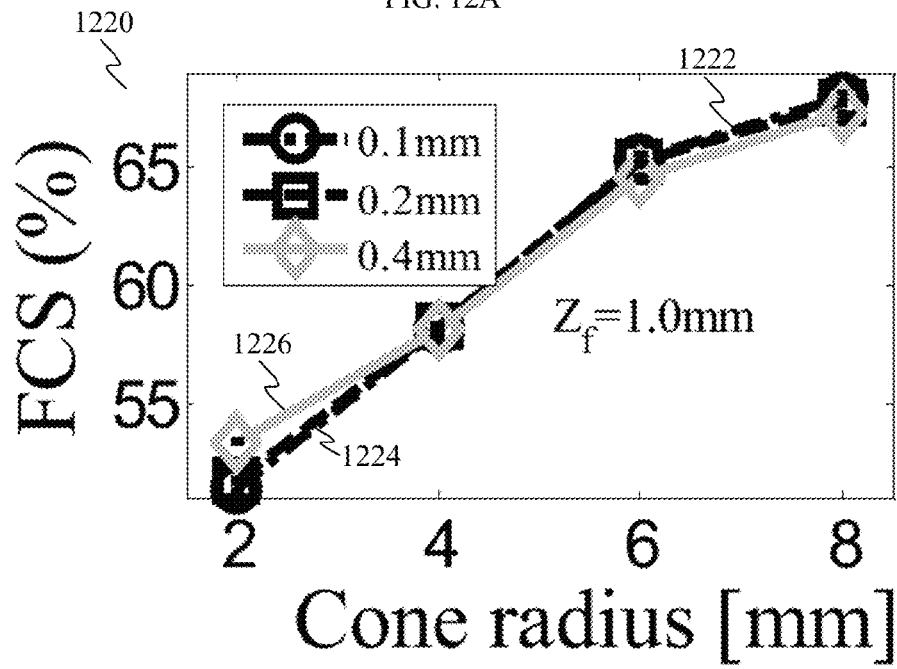
FIG. 12B shows a plot illustrating fraction of collisions in the stroma layer of the tissue model of FIG. 6 in a cone configuration (based on detection fiber size).

The depth sensitivity for the cone configuration in both illumination and detection is shown in FIGS. 12A and 12B based on the fraction of collision in the tumor (plot 1200) and the fraction of collision in the stroma (1220), respectively. As shown in FIGS. 12A and 12B, each line represents the results for a different detection fiber size as indicated in the legends. In FIG. 12A, plot line 1202 represents the detection fiber size being about 0.1 mm, plot line 1204 represents the detection fiber size being about 0.2 mm, and plot line 1206 represents the detection fiber size being about 0.4 mm. In FIG. 12B, plot line 1222 represents the detection fiber size being about 0.1 mm, plot line 1224 represents the detection fiber size being about 0.2 mm, and plot line 1226 represents the detection fiber size being about 0.4 mm.

In FIG. 12A, the depth of focal point in the tissue model, e.g. $Z_f$, is about 0.3 mm; while in FIG. 12B, the depth of focal point in the tissue model, e.g. $Z_f$, is about 1.0 mm.

FIG. 12A shows that a smaller detection fiber size may provide a higher fraction of collisions in the tumor region. FIG. 12B shows that the changes in the fraction of collisions in the stroma may be insignificant.

Depth sensitivity in a hybrid configuration with the cone shell illumination and cone detection will now be described.

Figure 13A:
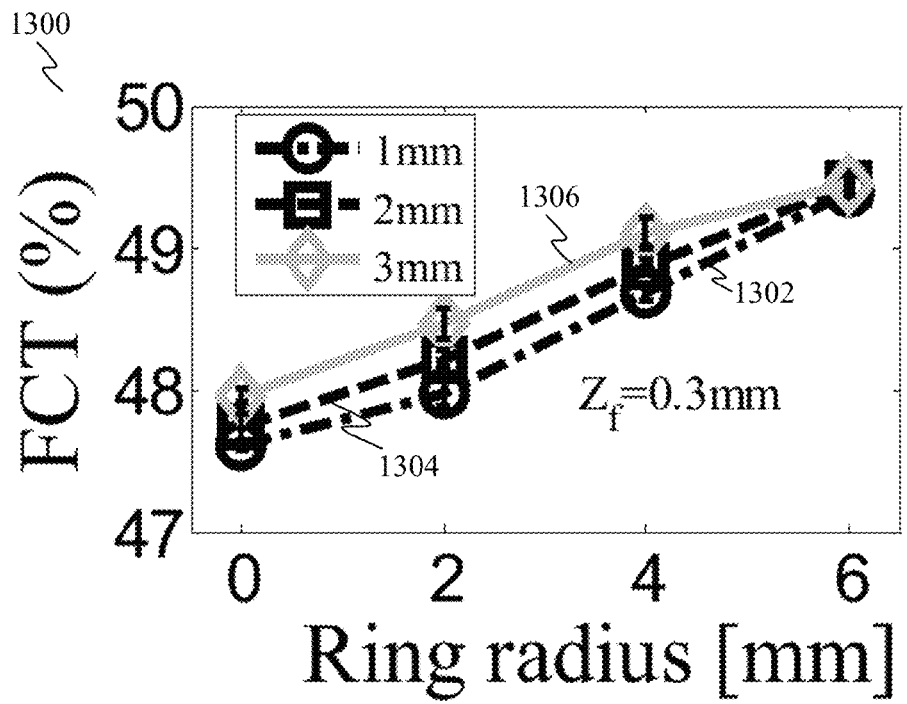
FIG. 13A shows a plot illustrating fraction of collisions in the tumor of the tissue model of FIG. 6 in a hybrid configuration (based on ring thickness), according to various embodiments.
Figure 13B:
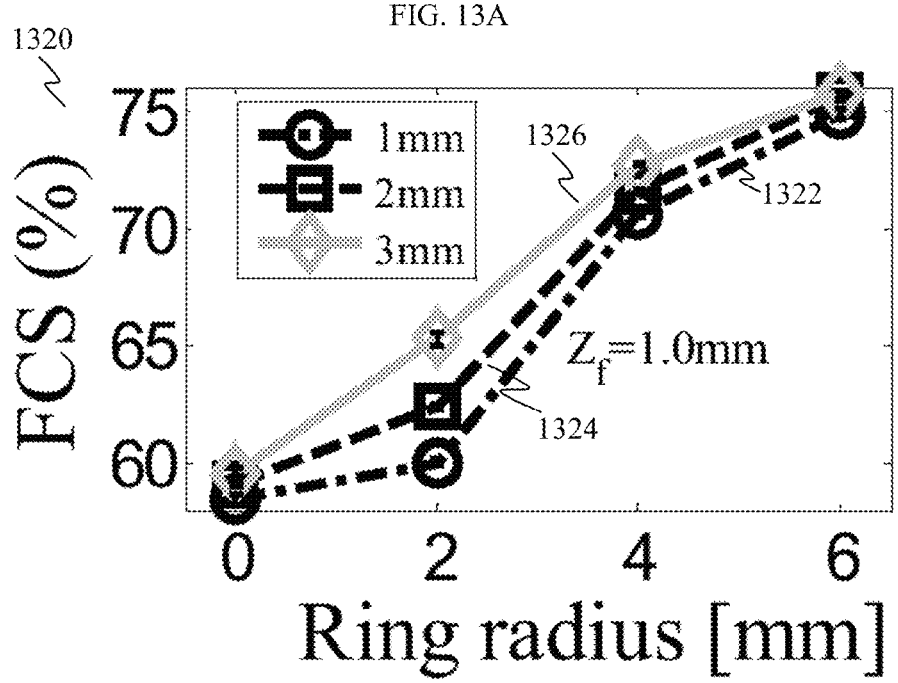
FIG. 13B shows a plot illustrating fraction of collisions in the stroma layer of the tissue model of FIG. 6 in a hybrid configuration (based on ring thickness), according to various embodiments.

FIGS. 13A and 13B show the effect of the ring thickness on the depth sensitivity of the hybrid configuration based on the fraction of collision in the tumor (plot 1300) and the fraction of collision in the stroma (plot 1320).

As shown in FIGS. 13A and 13B, each line represents the results for a different ring thickness as indicated in the legends. The diameter of the detection fiber may be fixed at about 0.2 mm. The radius of the cone for detection may be equal to the radius of the imaging lens, e.g. about 10 mm. In FIG. 13A, plot line 1302 represents the ring thickness being 1 mm, plot line 1304 represents the ring thickness being about 2 mm, and plot line 1306 represents the ring thickness being about 3 mm. In FIG. 13B, plot line 1322 represents the ring thickness being about 1 mm, plot line 1324 represents the ring thickness being about 2 mm, and plot line 1326 represents the ring thickness being about 3 mm.

In FIG. 13A, the depth of focal point in the tissue model, e.g. $Z_f$, is about 0.3 mm; while in FIG. 13B, the depth of focal point in the tissue model, e.g. $Z_f$, is about 1.0 mm.

FIGS. 13A and 13B show that a larger ring thickness may provide a slightly higher fraction of collisions in the tumor region and the stroma, but the changes in the fraction of collisions may not be significant.

Figure 14A:
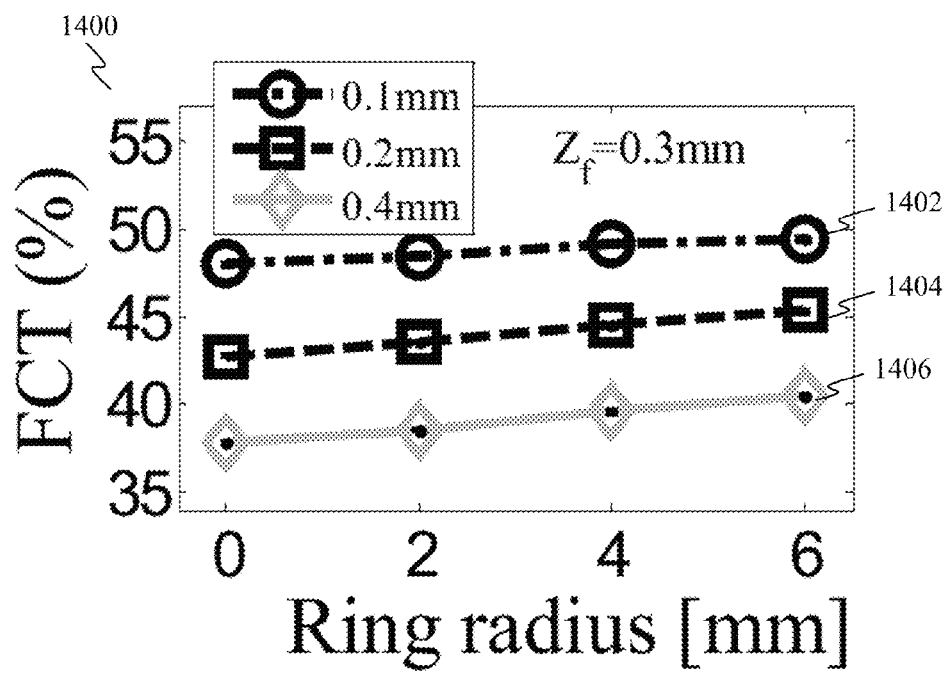
FIG. 14A shows a plot illustrating fraction of collisions in the tumor of the tissue model of FIG. 6 in a hybrid configuration (based on detection fiber size), according to various embodiments.
Figure 14B:
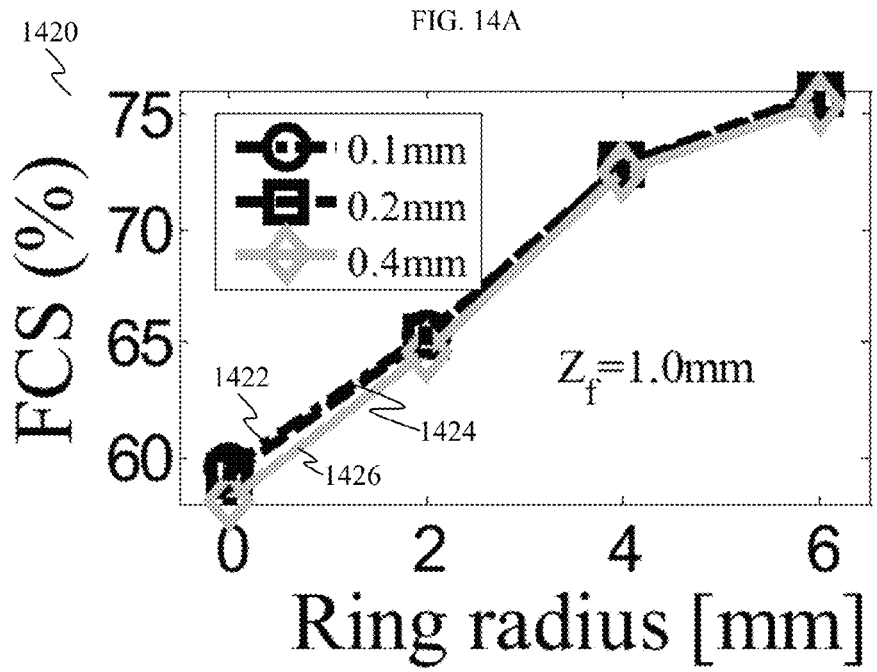
FIG. 14B shows a plot illustrating fraction of collisions in the stroma layer of the tissue model of FIG. 6 in a hybrid configuration (based on detection fiber size), according to various embodiments.

FIGS. 14A and 14B demonstrate the effect of the size of the detection fiber on the depth sensitivity of the hybrid configuration based on the fraction of collision in the tumor (plot 1400) and the fraction of collision in the stroma (plot 1420).

As shown in FIGS. 14A and 14B, each line represents the results for a different size of the detection fiber as indicated in the legends. The ring thickness may be fixed at about 3 mm. The radius of the cone for detection may be equal to the radius of the imaging lens, e.g. about 10 mm. In FIG. 14A, plot line 1402 represents the size of the detection fiber being about 0.1 mm, plot line 1404 represents the size of the detection fiber being about 0.2 mm, and plot line 1406 represents the size of the detection fiber being about 0.4 mm. In FIG. 14B, plot line 1422 represents the size of the detection fiber being about 0.1 mm, plot line 1424 represents the size of the detection fiber being about 0.2 mm, and plot line 1426 represents the size of the detection fiber being about 0.4 mm.

In FIG. 14A, the depth of focal point in the tissue model, e.g. $Z_f$, is about 0.3 mm; while in FIG. 14B, the depth of focal point in the tissue model, e.g. $Z_f$, is about 1.0 mm.

FIG. 14A shows that a smaller detection fiber size may provide a higher collision fraction in the tumor region. FIG. 14B illustrates a similar trend in the fraction of collisions in the stroma but the changes may be insignificant.

Comparison of depth sensitivity between the cone shell, cone and hybrid configuration will now be described.

Tables 5 and 6 show the comparison of the best sensitivity between all above configurations for the tumor and the stroma, respectively. The data in the table are extracted from the relevant figures (e.g. FIGS. 8 to 14).

TABLE 5

The best FCT between the cone, the hybrid and the cone shell set up for a depth of focus of about 0.3 mm

| Configuration | | Cone | Hybrid | Cone shell |
|---|---|---|---|---|
| Specifications | Radius | 8 mm | 6 mm | 6 mm |
| | Detector size | 0.1 mm | 0.1 mm | 0.1 mm |
| | Ring thickness | NA | 3 mm | 2 mm |
| | FCT | 49% ± 0.1% | 49% ± 0.1% | 51% ± 0.1% |
| | TC | 24.9% ± 0.4% | 29.9% ± 0.4% | 31.0% ± 0.6% |

Note:
FCT: The fraction of collisions in the tumor; NA: Not applicable; TC: tumor contrast. The row header "radius" refers to the cone radius in the cone configuration and the ring radius in both the cone shell configuration and hybrid configuration. In the rows of "FCT" and "TC", the first percentage is the mean while the second percentage is the standard deviation of the corresponding quantity.

TABLE 6

The best FCS between the cone, the hybrid and the cone shell set up for a depth of focus of about 1.0 mm

| Configuration | | Cone | Hybrid | Cone shell |
|---|---|---|---|---|
| Specifications | Radius | 8 mm | 6 mm | 6 mm |
| | Detector size | 0.1 mm | 0.4 mm | 0.4 mm |
| | Ring thickness | NA | 3 mm | 3 mm |
| | FCS | 68% ± 0.2% | 76% ± 0.2% | 74% ± 0.1% |

Note:
FCS: The fraction of collisions in the stroma; NA: Not applicable. The row header "radius" refers to the cone radius in the cone configuration and the ring radius in both the cone shell configuration and hybrid configuration. In the rows of "FCS", the first percentage is the mean while the second percentage is the standard deviation of the corresponding quantity.

Besides FCT and FCS, a new criterion, e.g. tumor contrast (TC), may be included to evaluate the sensitivity to tumor because of the general interest in tumor detection. The tumor contrast (TC) may be defined as the percent deviation for diffuse reflectance which may be calculated based on Eq. (14), $$TC = \frac{|R_{tumor} - R_{control}|}{R_{control}} \times 100\%, \quad \text{(Equation 14)}$$

where $R_{tumor}$ is the diffuse reflectance simulated from the tumor model and $R_{control}$ is the diffuse reflectance simulated from the control tissue model.

The two models may be exactly identical except that there may be no tumor buried in the epithelial layer in the control tissue model. Table 5 shows that there may be no significant difference between any two of the three configurations in terms of FCT. However, the hybrid configuration and the cone shell configuration may perform noticeably better than the cone configuration in terms of TC. Table 6 shows that the hybrid configuration and the cone shell configuration may yield similar FCS for the stroma, and both may perform better than the cone configuration.

The findings shown in the results above may be explained by considering the light transport in the tissue model as follows.

FIG. 7 shows the simulated diffuse reflectance as a function of the ring radius for a range of depths of focal point in the tissue model for the cone shell configuration. A depth of about 0.3 mm may produce the highest diffuse reflectance intensity in all cases, while a depth of about 1 mm may yield the lowest diffuse reflectance due to the larger attenuation associated with the longer photon path length in this case. Because a depth of about 1 mm may yield a high sensitivity to the stroma according to FIGS. 8 and 9, a tradeoff may have to be made between the diffuse reflectance intensity and the sensitivity to the stroma for the choice of the depth value. A similar tradeoff may need to be made between the diffuse reflectance intensity and the sensitivity to the tumor for the choice of the ring radius in the cone shell configuration.

In contrast, no tradeoff may be needed to be made for the choice of the depth value for the tumor because a depth of about 0.3 mm may yield both high sensitivity to the tumor and high diffuse reflectance intensity.

FIGS. 8A and 8B show that depth sensitive diffuse reflectance measurements may be achieved by adjusting: (1) the depth of the focal point in the tissue model; and/or (2) the cone radius in the cone configuration or the ring radius in the cone shell configuration. When the focal point of the imaging lens is located inside the tumor, e.g. $Z_f$=0.3 mm, most launched photons may reach and travel in the tumor region and the fraction of collisions spent in the tumor may be large. When the focal point is located in the stroma, e.g. $Z_f$=1.0 mm, most launched photons may travel around the tumor and reach the stroma due to the high anisotropy factor of the tumor and the epithelium, e.g. about 0.97.

Consequently, the fraction of collisions spent in the tumor may be significantly small and the fraction of collisions spent in the stroma may be large. It may be observed in FIG. 8A that a larger ring radius may yield a higher tumor collision fraction for a depth of the focal point of about 0.3 mm. The opposite trend may be observed for a depth of about 1.0 mm. This phenomenon may be explained by FIGS. 15A and 15B, in which the intersection between the cone shell region and tumor (drawn in black) may determine the contribution of the tumor to the measured diffuse reflectance.

Figure 15A:
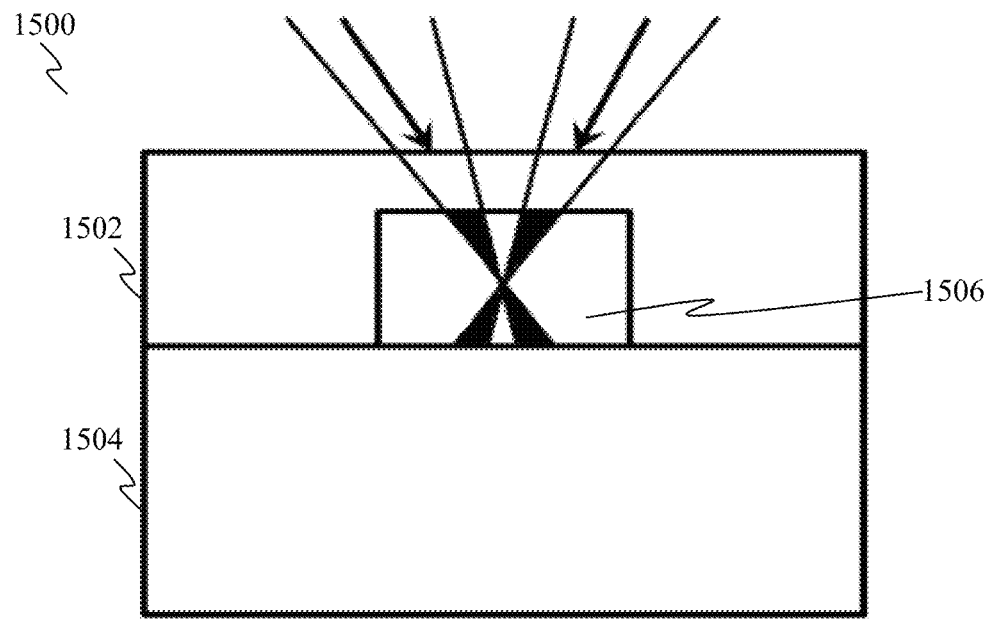
FIG. 15A shows a schematic cross-sectional side view of a squamous cell carcinoma tissue model illustrating the intersection of the cone shell region and the tumor with the depth of the focal point in the tumor model being 0.3 mm, according to various embodiments.

As shown in the schematic view 1500 of FIG. 15A, a focal point with a depth of about 0.3 mm may be located inside the tumor region 1506. When the ring radius is increased, the intersection of the cone shell region and the tumor 1506, e.g. the black area in FIG. 15A, may increase thus the fraction of collisions of detected photons spent in the tumor 1506 may increase accordingly. For a focal point with a depth of about 1.0 mm, the beam may travel through the epithelium 1502 and get around the central portion of the tumor 1506 and reach the tumor 1506 as shown in the schematic view 1520 of FIG. 15B. The intersection between the cone shell region and the tumor may be small thus few detected photons may travel through the tumor 1506. That may explain the small fraction of collisions in the tumor 1506 when the depth of the focal point is about 1.0 mm. The results for the fraction of collisions in the stroma as in FIG. 8C may be explained in a similar way.

FIGS. 10 and 13 both show that a cone shell configuration or a hybrid configuration with a thicker ring may perform slightly better in depth sensitivity regardless of the depth of the focal point. This may be explained as follows. For a small depth such as about 0.3 mm, the angle between the light beam and the normal axis may be larger when the ring is thicker. The intersection between the cone shell region and the tumor 1606 may thus be larger as shown in the schematic view 1600 of FIG. 16, so the depth sensitivity for tumor measurement may be better. Similarly, for a large depth of the focus such as about 1.0 mm, the intersection between the cone shell region and the tissue model may mainly be located within the stroma 1604. A thicker ring may mean more contribution from the stroma 1604.

Figure 16:
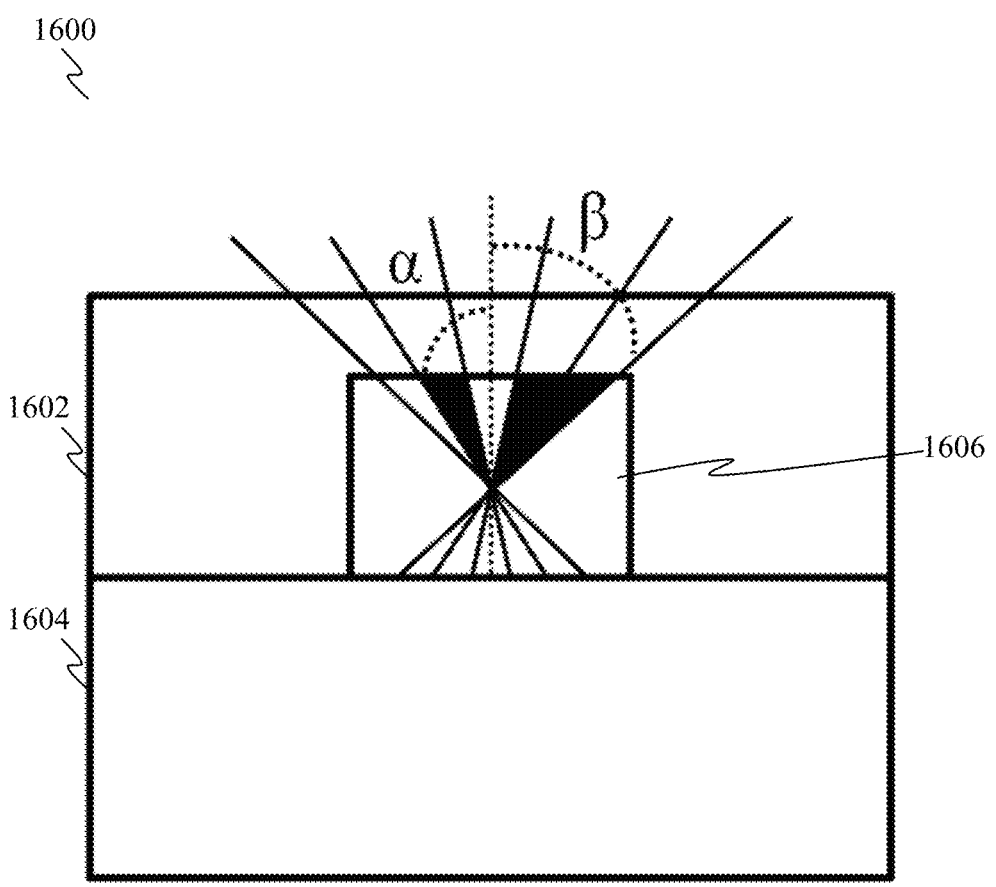
FIG. 16 shows a schematic cross-sectional side view of a squamous cell carcinoma tissue model illustrating the intersection of the cone shell region and the tumor with different ring thickness, according to various embodiments.

In FIG. 16, the symbols "α" and "β" refer to the angles between the light beam (which travels by the epithelium 1602) and the normal axis for a thin and a thick ring, respectively.

Figure 15B:
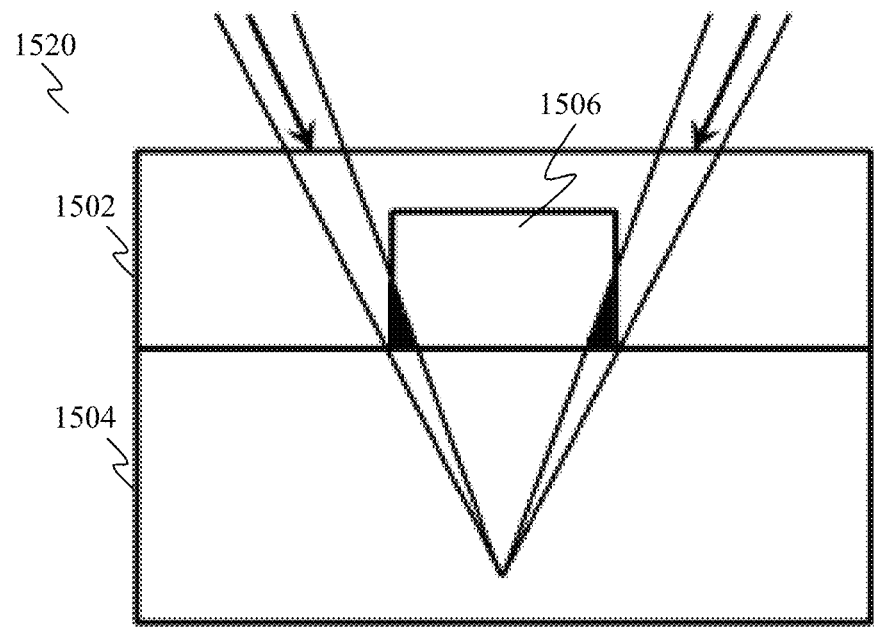
FIG. 15B shows a schematic cross-sectional side view of a squamous cell carcinoma tissue model illustrating the intersection of the cone shell region and the tumor with the depth of the focal point in the tumor model being 1.0 mm, according to various embodiments.

It should be appreciated that the interpretation by FIGS. 15A, 15B, and 16 may rely on the assumption that photons may roughly or approximately maintain the original direction before reaching the target region. This may be true if the desired depth is comparable to or smaller than the reciprocal of the reduced transport coefficient.

FIGS. 11A, 12A, and 14A show that a smaller detection fiber may perform better for a depth of the focal point at about 0.3 mm, which may be explained as follows. The detection fiber may be imaged into the tumor region according to the ray retracing method as shown in FIGS. 4A and 4B.

The image of a smaller fiber in the tumor region may more likely yield photons traveling in the tumor region thus a higher fraction of collisions in the tumor. In contrast, the image of a larger detection fiber may more likely yield photons traveling in other regions thus a smaller fraction of collisions in the tumor.

Tables 5 and 6 show that the cone shell and the hybrid configurations may perform better than the cone configuration in terms of sensitivity. For sensitive measurements from tumor, a cone shell configuration and a hybrid configuration with a large ring radius may yield much better performance than the cone configuration. This may be attributed to the fact that the cone shell configuration and the hybrid configuration may provide a relatively larger intersection between the cone shell region and the tumor compared to the cone configuration. The comparison between the cone shell configuration and the cone configuration may be analogous to that between a fiber-optic probe configuration with two obliquely placed fibers and that with two straight fibers to certain extent. For sensitive measurements from the stroma, a cone shell configuration or a hybrid configuration with a large ring radius may yield much better performance than the cone configuration. This may be due to the fact that the light beam in the cone shell configuration or the hybrid configuration may be able to propagate around the finite-width tumor and reach the stroma thus maximizing the contribution of the stroma to measured diffuse reflectance.

Another parameter that may affect simulation results may be the emission wavelength. The simulations described above are carried out for a wavelength of about 420 nm, which is close to the absorption peak of hemoglobin. The scattering coefficient of the tumor and the absorption coefficient of the stroma at about 420 nm may be particularly high, thus an enhanced sensitivity to the embedded tumor and the stroma may be achieved if the optimal configuration is used. At longer wavelengths, the scattering coefficient of the tumor and the absorption coefficient of the stroma may decrease. It may be quite likely that it may be more challenging to achieve the enhanced sensitivity to the tumor or the stroma. In that case, another series of simulations may be needed to find the exact sensitivities.

Although the tumor size may be fixed at a small value to represent an early tumor, the rules of thumb for achieving enhanced sensitivity to different regions may remain unchanged even if the tumor size changes because they agree with the analysis of illumination and detection geometry based on light propagation as shown in FIGS. 15A, 15B, and 16. Simulation of fiber-optic probes with related geometries may support the above analysis. The exact sensitivity to each region may change with the tumor size, which may be obtained by a new batch of simulations.

The central line of the Lens 2 210 and Lens 3 214 (FIG. 2A) may overlap with the middle line of the tumor. It may be predicted that the sensitivity to the lesion may decrease when the focal point is located on the margin of a lesion. In an application, the focal point may be scanned across a tumor in the lateral dimension with a small step size. During scanning, some measurements may be taken from the middle of the lesion and others may be taken from the margin of the lesion or outside the lesion. The difference between these measurements as quantified by "Tumor contrast" defined in Equation 14 may be used to find the tumor margin. The optimal configuration may maximize such a difference to increase the contrast of the tumor region relative to the normal region.

The method for simulating lens based illumination and detection may generally be applicable to any similar lens based setups for optical measurements. In addition, the following may be of applicable to any applications in which high sensitivity to a target tissue region is desirable. Based on the results shown above, it may be seen that the two parameters, e.g. the depth of focal point in the tissue model and the cone (in the cone configuration) or the ring (in the cone shell configuration) radius, may be of interest so as to achieve sensitive measurements from a given region. To achieve enhanced sensitivity to a target region, the focal point may need to be located in the region. Moreover, a large cone or ring radius, which may correspond to a small f-number for a fixed focal length, may help to achieve high sensitivity. These may be applicable to a layer tissue model with different optical properties if the desired depth is comparable to or smaller than the reciprocal of the reduced transport coefficient. This condition may ensure that photons may roughly maintain the original direction before reaching the target region.

Lens based setups as described above may be used for non-contact diffuse reflectance measurements to reduce the uncertainty due to inconsistent probe-sample pressure. A flexible Monte Carlo method may be used to model non-contact diffuse reflectance measurements in a lens based setup, as described above. This method may be used to simulate diffuse reflectance measurements from a squamous cell carcinoma (SCC) tissue model in the cone shell, cone and hybrid configurations, for optical spectroscopy.

As described above, depth sensitive measurements may be achieved by adjusting the following one or both parameters: (1) the depth of focal point of the imaging lens in the SCC model; and/or (2) the cone radius in the cone configuration or the ring radius in the cone shell configuration. The cone shell and the hybrid configurations may have better depth sensitivity to the tumor and the stroma than the cone configuration for diffuse reflectance measurements in the SCC model. The Monte Carlo method and the findings for different configurations may be useful in guiding the development of a noncontact lens based system for the optical diagnosis of early epithelial cancer.

The cone shell configuration as described above may yield larger depth sensitivity to deep layers than the cone configuration in diffuse reflectance measurements from a numerical model of squamous cell carcinoma. However, such a cone shell configuration may require the alteration of distance between the imaging lens and the tissue sample in order to achieve depth-sensitive measurements, which may induce uncertainty in optical coupling and inconvenience in clinical measurements.

As a non-limiting example, further embodiments of the cone shell illumination and collection configuration will now be described. The cone shell illumination and collection configuration may be based on a combination of multiple axicon lenses to address the drawback of the cone configuration in limited depth sensitivity to deep layers as well as to avoid or eliminate the need of altering the lens-sample distance in depth-sensitive measurements. The same configuration may also be applied in other optical measurements such as diffuse reflectance or Raman measurements.

Figure 17A:
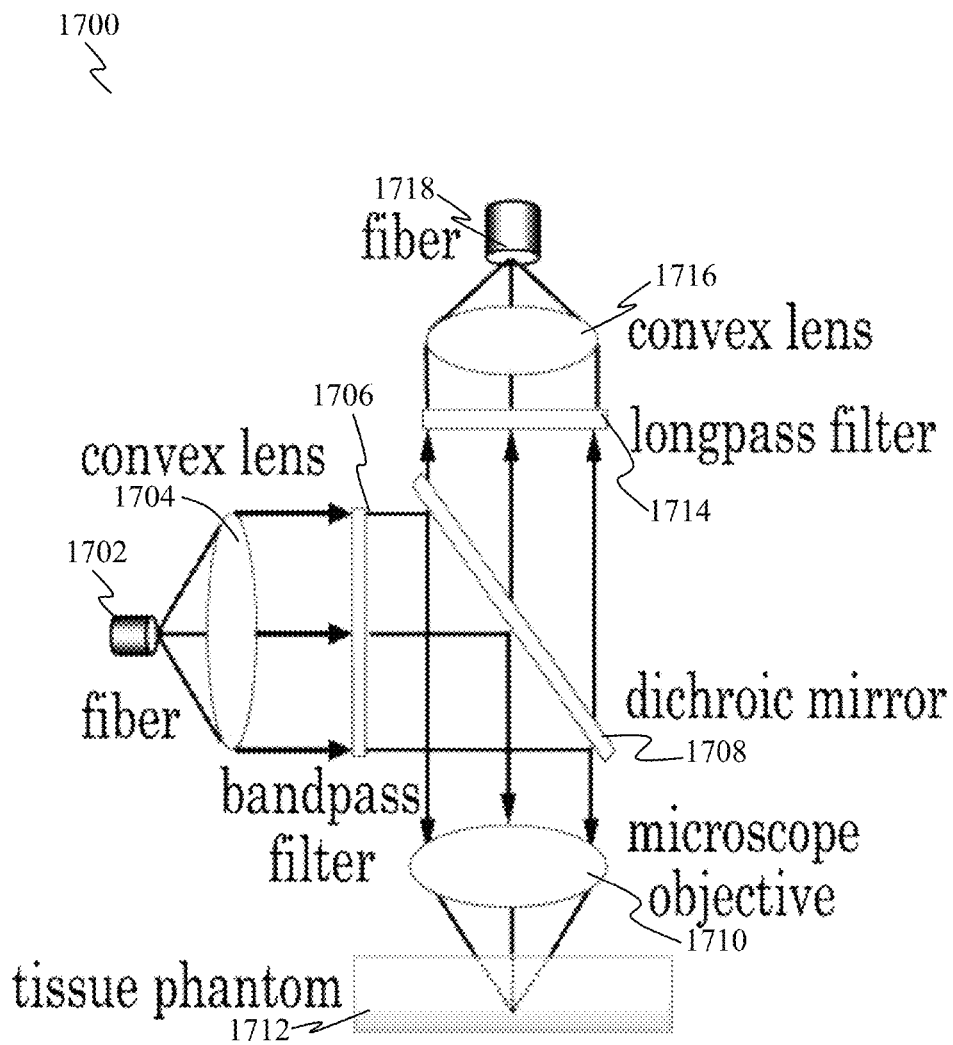
FIG. 17A shows a schematic side view of an optical setup of a cone illumination and detection configuration based on a microscope objective lens.

A fluorescence probe with a conventional cone illumination and detection configuration is shown in a schematic view 1700 of FIG. 17A. The probe may be coupled to a diode laser (not shown in FIG. 17A) through a single-mode fiber 1702 with a maximum output power of about 30 mW at a wavelength of about 405 nm. The output laser light may be collimated using a convex lens 1704 (f=50.0 mm) to achieve a beam diameter of about 6 mm before passing through a 405 nm band-pass filter 1706 and may be deflected by a dichroic mirror 1708 towards a microscope objective lens 1710 (10×, NA=0.25) onto a tissue phantom 1712 (or sample). The fluorescence signal may be collected through the same objective lens 1710, which may then pass through a long pass filter 1714 before being focused onto the tip of a collection fiber 1718 with a core diameter of about 400 μm and an NA of about 0.22.

Figure 17B:
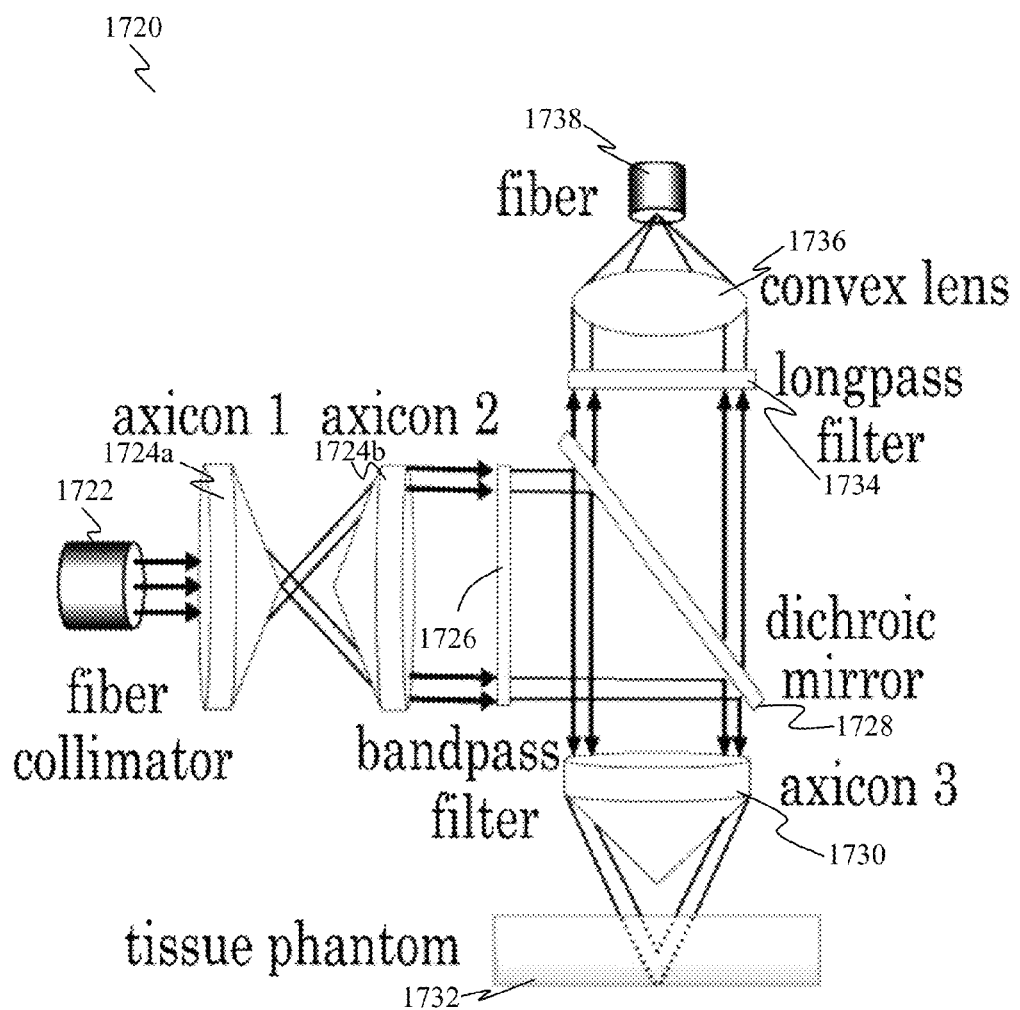
FIG. 17B shows a schematic side view of an optical setup of a cone shell configuration based on a combination of axicon lenses, according to various embodiments.

FIG. 17B shows a schematic view of a set-up 1720 having a cone shell configuration. As shown in FIG. 17B, a collimated laser beam of about 3 mm in diameter of a fiber collimator 1722 may be passed through a pair of axicon lenses, e.g. axicon 1 1724a and axicon 2, 1724b, with an identical apex angle of about 140° to create a donut-shape laser ring (annular illumination pattern). The laser ring may then be passed through a band-pass filter 1726 and may be deflected by a dichroic mirror 1728 towards a third axicon lens, e.g. axicon 3 1730. The laser ring may then be focused onto the sample (or tissue phantom 1732) by axicon 3 1730, with an apex angle of about 110°, forming the cone shell geometry. The fluorescence signal may come back through axicon 3 1730 and a long pass filter 1734 and may then be focused onto a collection fiber 1738, similar to the cone configuration. The fluorescence signals transmitted by the collection fiber 1738 in both configurations may be coupled to a Czerny-Turner-type spectrograph equipped with a holographic grating (1200 groove/mm) and a research-grade CCD, which may yield a spectral resolution of about 0.1 nm. The integration time may be about 1 s. The laser powers on the sample (e.g. tissue phantom 1732) are measured to be about 10 mW and about 7 mW for the cone and the cone shell configurations, respectively.

A two-layered agar phantom 1732 may be fabricated to mimic the stratified structure of human skin. The thickness of the top layer may be about 1 mm, and the thick ness of the bottom layer may be about 10 mm, whereas the lateral dimension of both layers may be made greater than about 30 mm in diameter to represent a semi-infinite medium. Two different endogenous fluorophores, flavin adenine dinucleotide (FAD) and protoporphyrin IX (PpIX), may be added to the top and bottom layers of the phantom 1732 to discriminate fluorescence from the two layers, which may be facilitated by the nonoverlapping emission peaks of FAD and PpIX at about 525 and about 630 nm, respectively.

A concentration of about 33.2 μM for FAD and a concentration of about 32.3 μM for PpIX may be used so that the intensities of both emission peaks may fall within the same order of magnitude for the ease of data analysis. A piece of plastic wrap may be placed between the two layers to prevent the diffusion of fluorophores between layers. Intralipid 20% may be added into each layer at a different concentration to mimic the light-scattering properties of the epidermis and dermis so that the reduced scattering coefficient, $\mu'_s$, may match a published value at about 525 nm. The published values for the reduced scattering coefficients for epidermis and dermis at 525 nm are about 63 cm$^{-1}$ and about 42 cm$^{-1}$, respectively. The optical properties of the phantom 1732 ($\mu'_s$ and $\mu_a$) at the excitation wavelength (about 405 nm) and peak emission wavelengths of PpIX (about 630 nm) may be estimated by extrapolating the optical properties of intralipid at a concentration of about 20% to obtain those for the concentration of intralipid used in various embodiments described herein.

Such extrapolation may assume that $\mu'_s$ and $\mu_a$ may be proportional to the concentration of intralipid. The optical properties of each layer of the phantom 1732 at the excitation and emission wavelengths are listed in Table 7.

TABLE 7

Optical Properties ($\mu_s'$ [cm$^{-1}$] and $\mu_a$ [cm$^{-1}$]) of the top and bottom layers for tissue phantom at the excitation wavelength and at the peak emission wavelengths of FAD and PpIX. $\mu_s'$ refers to the reduced scattering coefficient; $\mu_a$ refers to the absorption coefficient.

| Layer | Wavelength (nm) | | |
|---|---|---|---|
| | 405 (Excitation) | 525 (FAD) | 630 (PpIX) |
| Top | 80, 0.09 | 63, 0.03 | 55, 0.10 |
| Bottom | 51, 0.06 | 40, 0.02 | 35, 0.06 |

A range of apparent focal depths may be achieved by varying the lens-sample distance in the cone configuration as shown in FIG. 17A. A similar focal depth range may be achieved by varying the distance between the axicon lenses 1 and 2 1724*a*, 1724*b* in the cone shell configuration shown in FIG. 17B, which may minimize the variation in optical coupling. The targeted focal depths inside the tissue phantoms 1732 may be estimated by correcting for the refractive index mismatch between the phantom 1732 and air based on a refractive index of about 1.364 for the phantom 1732 and a refractive index of about 1 for air at about 405 nm.

Figure 18:
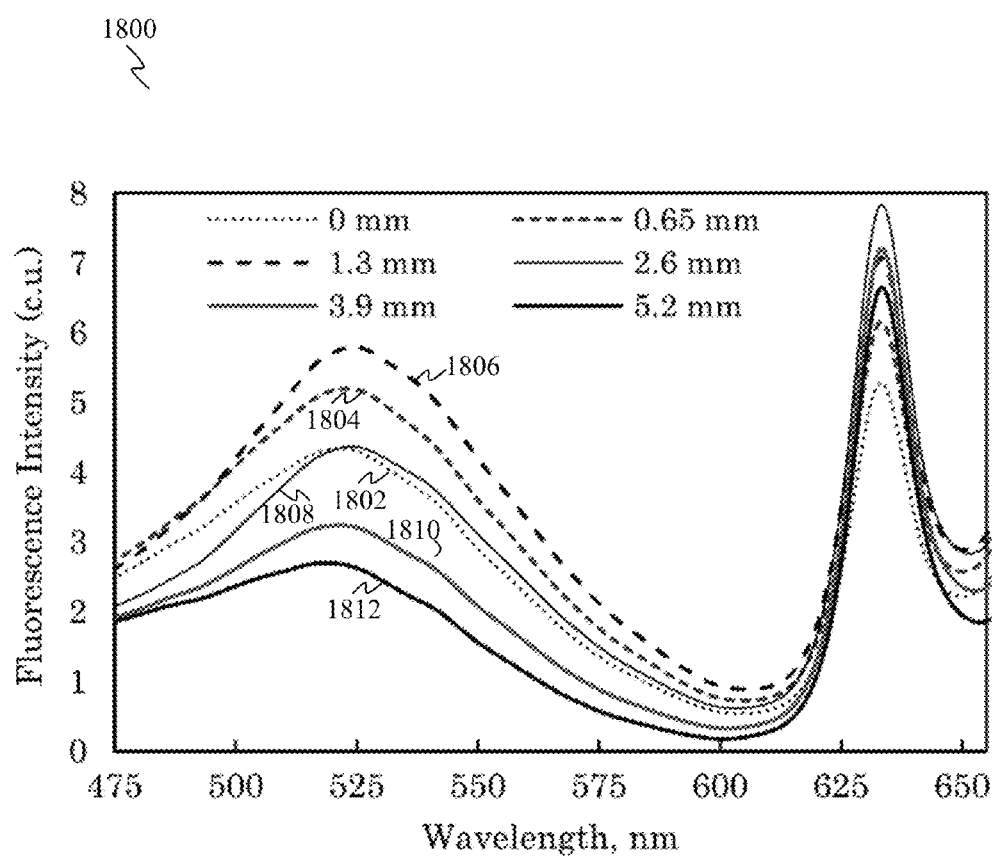
FIG. 18 shows a plot of fluorescence spectra measured using the cone shell configuration of FIG. 17B, according to various embodiments.

FIG. 18 shows a plot 1800 of the fluorescence spectra measured at a range of targeted focal depths from the two-layered phantom 1732 using the cone shell configuration corrected, as shown in FIG. 17B, for refractive index mismatch. In FIG. 18, the fluorescence intensity in "c.u." (referring to the calibrated unit) are determined at focal depths of 0 mm (plot line 1802), about 0.65 mm (plot line 1804), about 1.3 mm (plot line 1806), about 2.6 mm (plot line 1808), about 3.9 mm (plot line 1810), and about 5.2 mm (plot line 1812).

FAD fluorescence peak intensity (at about 525 nm) may gradually increase from the surface (0 mm) until reaching a maximum at a depth of about 1.3 mm and may decrease noticeably from about 1.3 mm to about 5.2 mm. PpIX fluorescence peak intensity (at about 630 nm) may also increase as the focal depth increases from 0 to about 2.6 mm and may decrease as the focal depth increases further. This trend, in which the peak intensity may increase to the maximum and then decrease, may be attributed to two factors. The first factor may be that the length of the line focus formed by axicon 3 1730 may be around 1.7 mm, which may cause half of the line focus to be still in air when the focal depth is zero. The second factor may be light attenuation due to the significant increase in light path length that may cause the detected fluorescence signal to decrease. While the first factor may prevent the maximum from occurring at zero focal depth, the second factor may push the maximum towards the surface. The combination of the two factors may imply that the maximum corresponding to each layer may occur in the middle of the layer as observed in FIG. 18. This may be consistently observed when a series of depth-sensitive measurements in a homogenous sample is performed. Fluorescence intensities corresponding to the top and bottom layers reached maxima at different focal depths, which may demonstrate that the cone shell configuration using axicon lenses may be capable of performing depth-sensitive fluorescence measurements without altering the lens-sample distance. To compare the sensitivity improvement achieved by this approach, the sensitivity of measured fluorescence to the top and bottom layer may be computed as a function of the targeted depth for both the cone and cone shell configurations as follows.

First, each raw FAD peak intensity measured at every depth may be divided by the maximum among these intensities to obtain normalized FAD intensities. Similarly, each raw PpIX peak intensity measured at every depth may be divided by the maximum among these intensities to obtain normalized PpIX intensities. Then, the sensitivity to the top layer at each depth may be calculated by dividing the normalized FAD intensity at this depth by the sum of normalized FAD and PpIX fluorescence intensities at this depth. Similarly, the sensitivity to the bottom layer at each depth may be calculated by dividing the normalized PpIX intensity at this depth by the sum of normalized FAD and PpIX fluorescence intensities at this depth.

Figure 19:
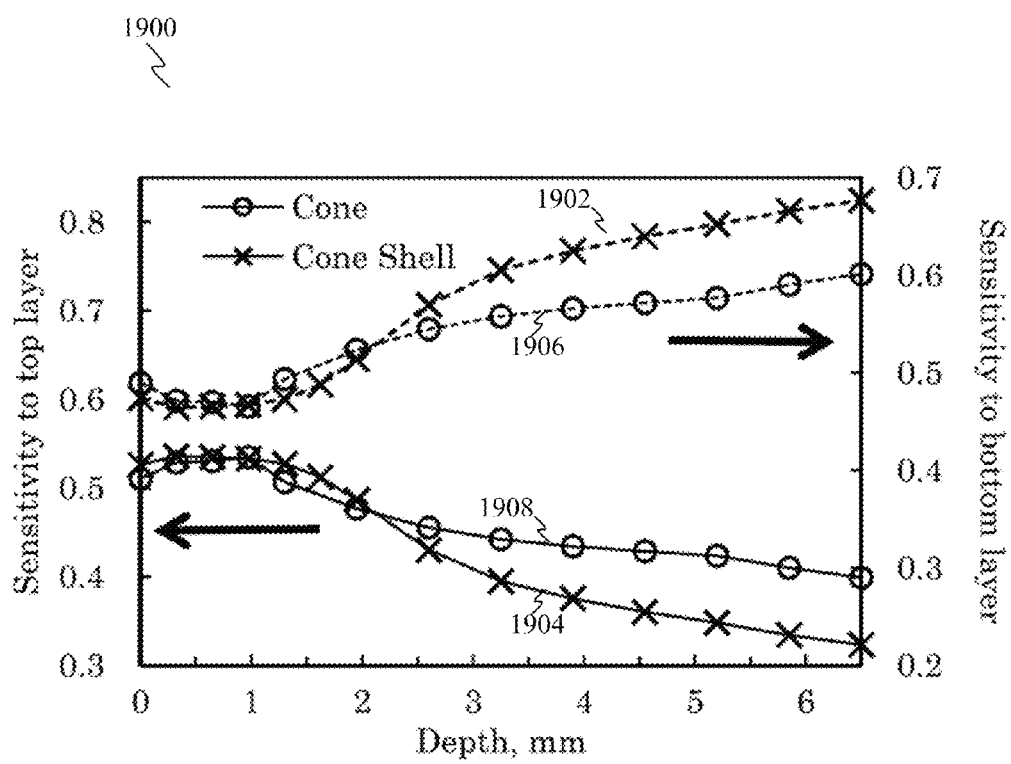
FIG. 19 shows a plot illustrating the sensitivity to layers as a function of the targeted depth of focus beneath a phantom surface of the tissue phantom shown in FIG. 17B, according to various embodiments.

FIG. 19 shows a plot 1900 illustrating sensitivity to the top and bottom layers as a function of the targeted depth of focus beneath the phantom surface 1732, which may be corrected for refractive index mismatch between the sample and air. "O" refers to the cone configuration; and "x" refers to the cone shell configuration. The solid lines and the dashed lines indicate the sensitivities to the top layer and the bottom layer, respectively.

For example, plot line 1902 refers to the sensitivities to the bottom layer in the cone shell configuration, plot line 1904 refers to the sensitivities to the top layer in the cone shell configuration, plot line 1906 refers to the sensitivities to the bottom layer in the cone configuration, and plot line 1908 refers to the sensitivities to the top layer in the cone configuration.

From FIG. 19, it may be observed that the maximum sensitivities of both the cone and cone shell configuration to the top layer may be around (or about) 0.53 but the maximum location of the cone configuration may have a narrower peak at about 0.98 mm, close to the actual thickness of the top layer. This may be explained by the difference in the focal spot size between the two configurations. The microscope objective lens 1719 (FIG. 17A) in the cone configuration may form a tiny (or small) focal spot of about 20.9 μm in diameter, which may be much smaller than the top layer thickness. In contrast, the axicon lens (e.g. axicon 3 1730 (FIG. 17B)) may form an elongated focal line of around about 1.7 mm in the axial dimension, which may be estimated using the Pythagoras theorem given that the thickness of the laser ring incident on axicon 3 1730 may be measured to be about 0.8 mm. Therefore the depth resolution of the cone configuration may be superior to that of the cone shell configuration. The minimum sensitivity to the top layer for the cone shell configuration, which may be about 0.32 at a focal depth of about 6.5 mm, may be lower than that for the cone configuration, which may be about 0.4 at the same focal depth. Therefore the range of the sensitivity to the top layer achieved with the cone shell configuration may be advantageously larger than that with the cone configuration. The maximum sensitivity to the bottom layer for the cone configuration, which may about 0.60 at a focal depth of about 6.5 mm, may be considerably lower than that for the cone shell configuration, which may be about 0.68 at the same focal depth. This depth may correspond to the minimum sensitivity to the top layer.

This observation may be attributed to the high possibility that the cone shell configuration may effectively reduce the illumination volume near the surface when focusing on a deep layer due to the absence of the light core in the volume. As a consequence, the contribution of fluorescence from the top layer may be effectively weakened, which may result in a higher maximum sensitivity to the bottom layer. Moreover, the range of the sensitivity to the bottom layer achieved with the cone shell configuration may also be advantageously larger than that with the cone configuration.

As described above, a noncontact setup to implement a cone shell illumination and detection configuration using axicon lenses for depth-sensitive fluorescence measurements may be provided. The cone shell configuration involving multiple axicon lenses may detect fluorescence with a higher sensitivity to the bottom layer and a larger range of sensitivity to either the top or the bottom layer in a two-layered tissue phantom mimicking human skin. In other words, the setup may be capable of detecting fluorescence from a two-layered turbid agar phantom with a larger sensitivity to the deep layer and a larger range of sensitivity to either layer than a typical cone configuration implemented by a microscope objective lens. Furthermore, the above features may be achieved without altering the distance between the imaging lens and the sample, which may minimize inconsistency and therefore may effectively improve the consistency in optical coupling and may bring significant convenience in potential clinical measurements, thus being preferred in a clinical setting.

Given the above advantages, depth sensitive measurements using the abovementioned setup of various embodiments may be somewhat challenging in terms of time inefficient as it may still require the change in the distance between two axicon lenses in the setup.

To address the time inefficiency issue described above, a non-limiting example of a method of improving the spectra acquisition speed of the axicon lenses based setup described above will now be described. A fiber assembly may be used, by incorporating five rings of collection fibers into the detection configuration, which may enable the collection of optical spectra from five different depths simultaneously. This setup may remove the need of the mechanical moving part including or consisting of two axicon lenses that may be required to achieve depth sensitive measurements. The performance of this improved setup may be evaluated in the same manner mentioned above for the axicon lens-based cone shell configuration for depth-sensitive fluorescence measurements.

Figure 20A:
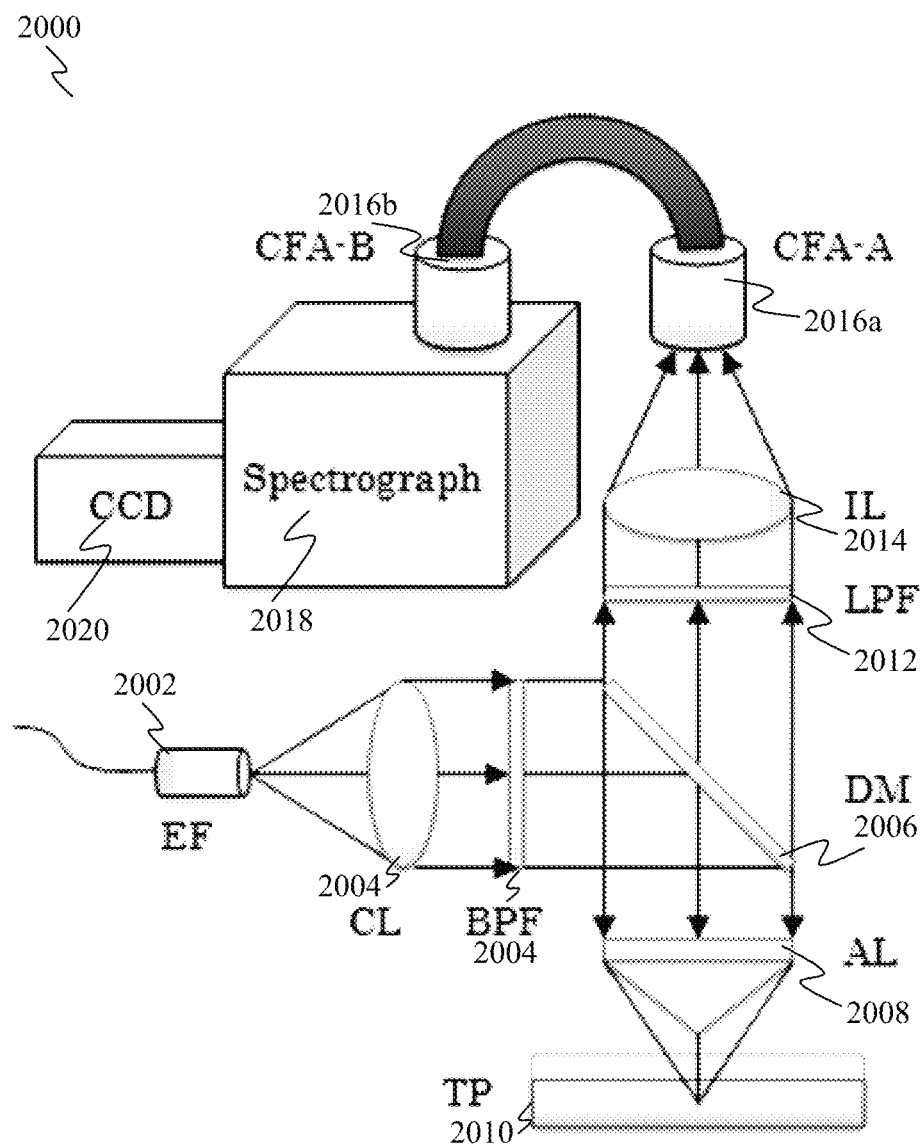
FIG. 20A shows a schematic side view of an optical setup of a cone shell configuration with detection using a fiber assembly, according to various embodiments.

A set-up having a fluorescence fiber assembly with five rings of collection fibers may be constructed as shown in a schematic view illustrated in FIG. 20A. A 405 nm diode laser (not shown in FIG. 20) coupled to a single-mode fiber (or excitation fiber EF) 2002 may be used to deliver excitation light with a maximum output power of about 30 mW. The output laser light may be collimated using a convex lens (e.g., collimating lens CL 2004) (f=75.0 mm) to achieve a beam diameter of about 9 mm. Then, the beam may be passed through a 405 nm bandpass filter BPF 2004 and a dichroic mirror DM 2006 and before focusing on the sample (e.g., tissue phantom TP 2010) by an axicon lens AL 2008, with an apex angle of 110°. The axicon lens 2008 may be fixed at a distance of about 0.89 mm above the sample surface. The fluorescence signal may be collected through the same axicon lens 2008 and may be passed through a long pass filter LPF 2012 before being imaged onto the tip of a custom designed fiber assembly by a convex lens (f=35.0 mm). The distance between this imaging lens, IL 2014, and the tip of the collection fiber assembly end B (CFA-B) 2016b may be adjusted to be about 28.5 mm.

For example, the fiber assembly may include 48 live fibers and 43 dead spacer fibers with core/cladding/coating diameters of 100/110/125 μm and a numerical aperture (NA) of about 0.22. Live fibers may be represented by similar dots 2042, 2044, 2046, 2048, 2050 while dead fibers may be represented by other similar dots 2052 in FIGS. 20B and 20C. Live fibers 2042, 2044, 2046, 2048, 2050 at end A 2016a of the fiber assembly may be symmetrically arranged into five rings (as represented by the dashed circles in FIG. 20B) surrounding a central spacer fiber, in which the number of collection fibers may be six (6), six (6), twelve (12), twelve (12) and twelve (12), respectively, from the inner to the outer ring. At end B 2016b of the fiber assembly, these live fibers 2042, 2044, 2046, 2048, 2050 may be arranged into five blocks each with six rows of fibers, and any two adjacent blocks of fibers may be vertically separated by about 530 μm. The first two blocks may have one fiber in each row while blocks 3, 4 and 5 may have two fibers in each row, as shown in FIG. 20C. From the top to the bottom of FIG. 20C, the five blocks may correspond to rings 1, 2, 3, 4 and 5 in the order from the inner ring to the outer ring.

The fluorescence signals collected by the fiber assembly may be directed to a Czerny-Turner type spectrograph, which may be equipped with a holographic grating (1200 grove/mm) (e.g., spectrograph 2018) and a research-grade CCD 2020 that may yield a spectral resolution of about 0.1 nm. The input slit of the spectrometer 2018 may be set to be 250-μm wide so as to allow the signals from fiber assembly end B 2016b to enter. The CCD 2020 may be horizontally divided into 5 regions that may be spaced apart vertically so that each region may cover one block on the fiber assembly end B 2016b. Photons reaching each CCD region may be binned vertically to produce five spectra corresponding to five individual fiber blocks for each measurement. The integration time may be about 0.5 second. The laser powers incident on the sample 2010 may be measured to be about 15 mW.

A two-layered agar phantom may be fabricated using the typical recipe and procedure. FAD may be added to the top layer at a concentration of 33.2 μM while PpIX may be added to the bottom layer at a concentration of 32.3 μM. FAD and PpIX may be chosen as the fluorophores because they are intrinsic biological fluorophores that may be be found inside tissue, with non-overlapping emission peaks at about 525 nm and about 630 nm, respectively. The dimension and optical properties of the phantom 2010 may be made identical to that as described above for tissue phantom 1732 (FIG. 17B).

During measurements, the collected signals that reach the imaging lens 2014 may be focused onto the tip of fiber assembly end A 2016a with an approximate demagnification factor of about 5.4. The axicon lens 2008 may be lifted to about 0.89 mm above the sample 2010 so as to prevent the superficial fluorescence signals from reaching the central dead fiber 2052 on the fiber assembly end A 2016a. Each ring of collection fibers on the collection fiber assembly may correspond to a different targeted depth in the tissue phantom 2010. The corresponding depth in the phantom 2010 for each fiber ring may be computed by Pythagoras Theorem with the beam deviation angle, β given by:

$$\beta = \sin^{-1}(n \cdot \sin \alpha) - \alpha \quad \text{(Equation 15)},$$

where the refractive index, n, of the axicon (N-BK7 glass) may be 1.53 at 405 nm.

The corresponding depths of measurements for each ring of fibers, which may be corrected for refractive index mismatch between the tissue phantom 2010 and the air are shown in Table 8.

TABLE 8

Radial distance of each ring of collection fibers from the centre of fiber assembly and the corresponding depth in phantoms after correction for refractive index mismatch.

| Ring | Radial distance on fiber assembly end B from the centre (mm) | Corresponding depth in sample after correction for refractive index mismatch (mm) |
|---|---|---|
| 1 | 0.125 | 0.00 |
| 2 | 0.250 | 1.16 |
| 3 | 0.375 | 2.32 |
| 4 | 0.500 | 3.47 |
| 5 | 0.625 | 4.63 |

The calculation may be based on the refractive indices of air and intralipid 20% at about 405 nm, which may be about 1 and about 1.364, respectively.

Figure 20B:
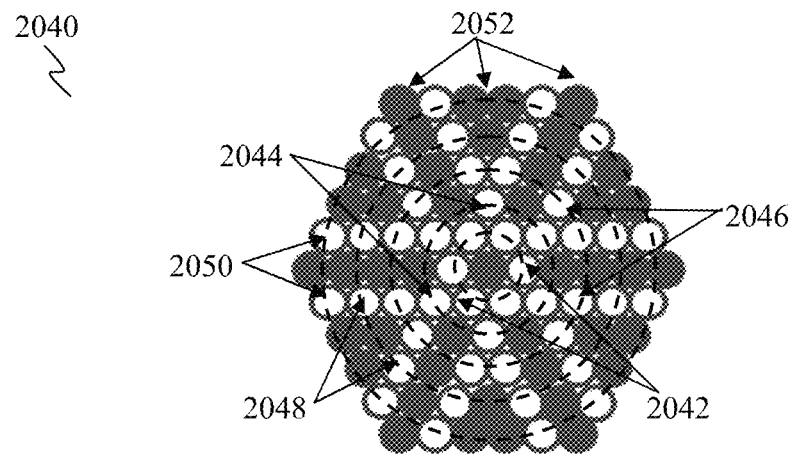
FIG. 20B shows a schematic cross-sectional view of one end of the fiber assembly of the optical setup of FIG. 20A, according to various embodiments.
Figure 21:
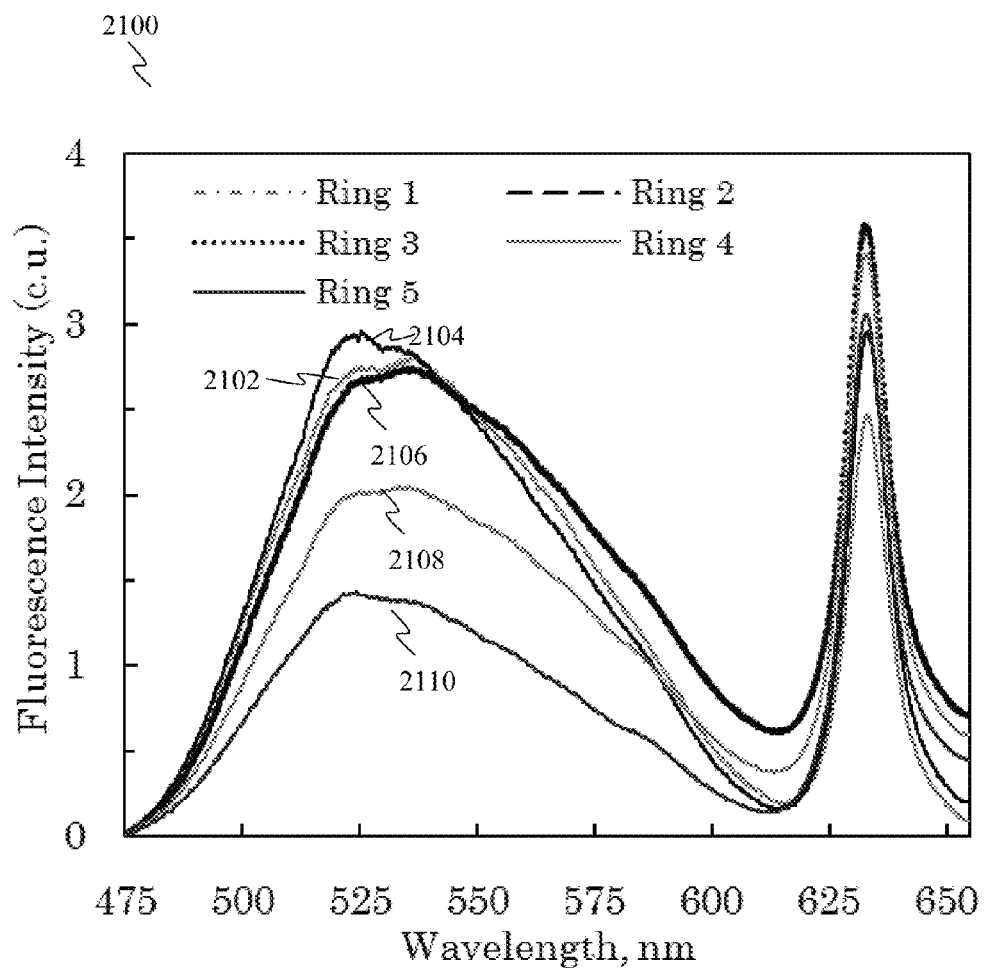
FIG. 21 shows a plot of fluorescence spectra measured using the fiber assembly of FIG. 20A, according to various embodiments.

FIG. 21 shows a plot 2100 of fluorescence spectra measured using the system of different rings of collection fibers from the two-layered phantom as shown in FIG. 20A. In FIG. 21, the abbreviation "c.u." refers to the calibrated unit. Each spectrum (e.g. plot lines 2102, 2104, 2106, 2108, 2110, respectively) may be measured from a different ring of fibers, labeled by the ring number from 1 to 5, e.g. Ring 1 2042 (FIG. 20B), Ring 2 2044 (FIG. 20B), Ring 3 2046 (FIG. 20B), Ring 4 2048 (FIG. 20B), and Ring 5 2050 (FIG. 20B), respectively, with an increasing distance from the assembly's centre as shown in Table 8. FAD peak intensity that may represent the fluorescence contribution from top layer increases from Ring 1 (see plot line 2102), which may correspond to the sample surface at 0 mm, to the maximum in Ring 2 (see plot line 2104), which may correspond to a targeted depth of about 1.21 mm beneath the surface. FAD peak intensity may then go down from Ring 3 (see plot line 2106) to Ring 4 (see plot line 2108) and reaches the minimum in Ring 5 (see plot line 2110). PpIX peak intensity that may represent the fluorescence contribution from the bottom layer may increase significantly from Ring 1 (see plot line 2102) to Ring 2 (see plot line 2104) and may reach the maximum in Ring 3 (see plot line 2106) which may correspond to a targeted depth of about 2.48 mm. Then, PpIX peak intensity may start to drop from Ring 4 (see plot line 2108) to Ring 5 (see plot line 2110). In both representative peak locations of FAD and PpIX, the peak intensity may increase to the maxima with an increasing targeted depth and may then decrease after that. The same trend may be observed and discussed as seen in FIG. 18. FAD and PpIX peak intensities may reach their maxima in different rings of collection fibers, which may show that this system may be capable of performing simultaneous depth sensitive fluorescence measurements from a range of targeted depths with no mechanical moving components and without altering the lens-sample distance.

To evaluate the performance of this system (FIG. 20A) in depth sensitive measurements, the sensitivities in fluorescence measurements to the top and bottom layers of this system may be computed as described below.

First, the raw spectra measured by the respective fibers of Ring 1 and Ring 2 may be multiplied by a ratio of 2, as the number of fibers in each of these rings are only half of the number of fibers in the outer three rings, so that the fluorescence intensities measured by all rings may have similar magnitudes. Then, the baseline subtraction may be performed on each spectrum. After that, the FAD peak intensity measured by each ring may be divided by the maximum of these peak intensities to obtain the normalized FAD intensities. Similarly, the PpIX peak intensity measured by each ring may be divided by the maximum among these peak intensities to obtain the normalized PpIX intensities. The sensitivity of fluorescence measurements to the top layer may then be computed by taking the ratio of the normalized FAD intensity measured by each ring to the sum of the normalized FAD and PpIX intensities measured by the same ring. The sensitivity of fluorescence measurements to the bottom layer may be calculated by taking the ratio of the normalized PpIX intensity measured by each ring to the sum of the normalized FAD and PpIX intensities measured by the same ring.

Figure 22:
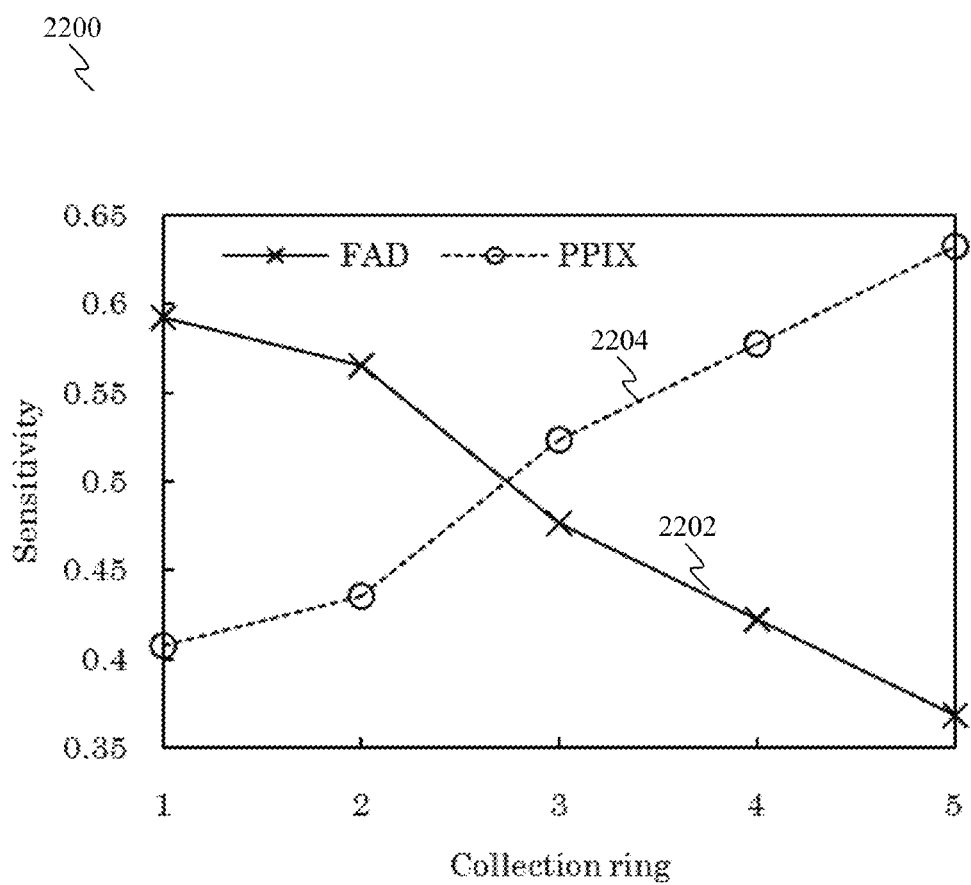
FIG. 22 shows a plot illustrating the sensitivity to layers with respect to the collections rings of the fiber assembly of FIGS. 20A and 20B, according to various embodiments.

FIG. 22 shows a plot 2200 illustrating the sensitivity of fluorescence measurements achieved by each collection ring in the system of FIG. 20A to the top and bottom layer of the tissue phantom 2010. In FIG. 22, the x-axis refers to collection rings where collection ring 1 (e.g. Ring 1 2042 of FIG. 20B) may refer to the ring of fibers with the smallest radial distance from the centre and collection ring 5 (e.g. Ring 5 2050 of FIG. 20B) may refer to the ring of fibers with the largest radial distance from the centre of the fiber assembly. It may be observed that the sensitivity to the top layer (FAD) for collection ring 1 (see plot line 2202) may be the highest at about 0.59, followed by collection ring 2 at about 0.56, collection ring 3 at about 0.48, collection ring 4 at about 0.42 and the lowest by collection ring 5 at about 0.37.

On the other hand, the sensitivity to the bottom layer for collection ring 1 (see plot line 2204) may be the lowest at about 0.41, followed by collection ring 2 at about 0.44, collection ring 3 at about 0.52, collection ring 4 at about 0.58 and the maximum by collection ring 5 at about 0.63. Compared to the top layer sensitivities for the axicon lenses based setup (FIG. 17B) ranging from about 0.36 to about 0.53, which may correspond to a targeted depth varying from 0 mm to about 4.6 mm, the top layer sensitivities for the improved setup (FIG. 20A) varied from about 0.37 (Ring 5) to about 0.59 (Ring 1) for the same range in the targeted depth. The sensitivities to the top layer at a targeted depth of about 4.6 mm in both setups may be similar but the maximum sensitivity to the top layer in the setup of FIG. 20A may increase by approximately 11.3%. Consequently, the bottom layer sensitivities of the setup of FIG. 17B at the targeted depth of 0 mm and about 4.6 mm may be about 0.47 and about 0.64 while those of the setup of FIG. 20A may be about 0.41 and about 0.63. This observation may indicate the achievement of a larger range of sensitivity to the bottom layer by the incorporation of collection fibers in multiple rings to the detection configuration.

Figure 20C:
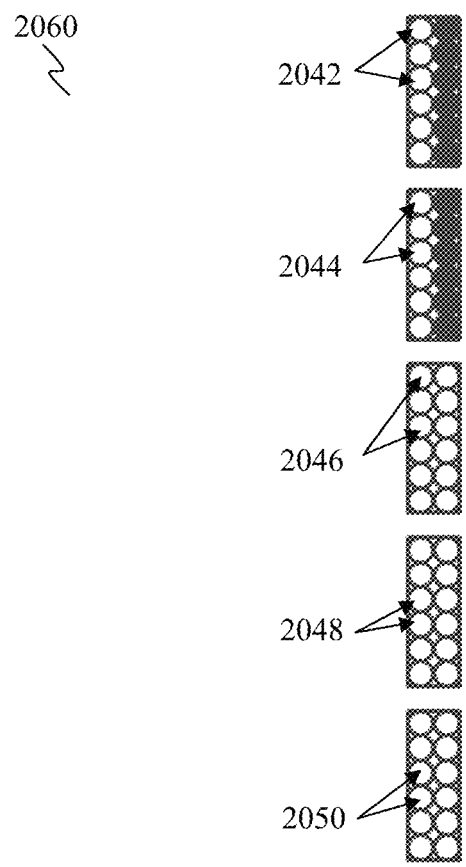
FIG. 20C shows a schematic cross-sectional view of an opposite end of the fiber assembly of the optical setup of FIG. 20A, according to various embodiments.

The improvement in the maximum sensitivity to the top layer in the improved setup compared to the setup of FIG. 17B may be attributed to the fact that the collection fibers in Ring 1 shown as the inner ring in FIG. 20B may serve as a photon gate that may block photons not originating from the targeted depth due to its limited numerical aperture. It may be speculated that those photons reducing the sensitivity to the top layer may mostly come from the deep layer through the tip of the axicon lens (e.g. 2008), since it may be known that the tip of an axicon lens may be rounded rather than sharply polished. A similar gating mechanism may not be present in the setup of FIG. 17B, thus a portion of those photons from the deep layer may be detected and may cause degradation in the sensitivity to the top layer.

As described above, various embodiments may enable depth-sensitive fluorescence spectroscopy in a sample (e.g. two-layered epithelial tissue phantom) using a cone shell configuration implemented by an axicon lens and a fiber assembly including five rings of collection fibers. The spectra acquisition speed of the axicon lenses based setup for depth sensitive optical measurements may be improved by incorporating the five rings of signal collection fibers into the detection configuration, which may enable the collection of optical spectra from five different depths simultaneously, and thus may shorten data acquisition significantly. Each collection fiber ring may be located at a different radial distance away from the centre, for which fluorescence measurements from all rings may show a larger range of sensitivities to the top and bottom layers compared to the cone shell configuration (based on FIG. 17B). This setup (as shown in FIG. 20A) may avoid or eliminate the need of a mechanical moving part including or consisting of two axicon lenses that may be required to achieve depth sensitive measurements. The setup may detect fluorescence with a higher sensitivity to the top layer and may achieve larger range of sensitivity to both the top and bottom layer in a two-layered turbid phantom. Inheriting the advantage of the setup of FIG. 17B, that is without the need of altering the lens-sample distance in performing depth sensitive measurements, this setup (FIG. 20A) may have enhanced depth sensitivity capability and improved acquisition speed, hence offering more significant convenience and better diagnostic performance in clinical measurements.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An optical detection device comprising:
an optics arrangement configured to generate an annular illumination pattern to illuminate a portion of a sample and further configured to receive a return light from the portion of the sample illuminated by the annular illumination pattern;
a detector arrangement configured to detect the return light; and
a fiber assembly arranged to receive the return light and to optically couple the return light to the detector arrangement,
wherein the fiber assembly comprises a plurality of dead fibers and a plurality of live fibers, wherein the plurality of dead fibers and the plurality of live fibers are arranged in a plurality of concentric patterns at one end of the fiber assembly to receive the return light;
wherein the plurality of live fibers are arranged in a plurality of linear blocks at an opposite end of the fiber assembly;
wherein the optics arrangement further comprises a light director arranged to optically couple the return light towards the detector arrangement;
wherein the fiber assembly is arranged between the detector arrangement and the light director;
wherein a number of linear blocks corresponds to a number of concentric patterns; and
wherein the live fibers of each concentric pattern are arranged in a respective linear block of the plurality of linear blocks so that each linear block of the plurality of linear blocks corresponds to one concentric pattern.

2. The optical detection device as claimed in claim 1, wherein the optics arrangement comprises shaping optics for receiving a light and shaping the light to generate the annular illumination pattern.

3. The optical detection device as claimed in claim 2, wherein the shaping optics comprises a first axicon lens and a second axicon lens, wherein the first axicon lens and the second axicon lens are further configured to collimate the annular illumination pattern.

4. The optical detection device as claimed in claim 3, wherein each axicon lens comprises a conical surface, wherein respective conical surfaces of the two axicon lenses are arranged facing each other.

5. The optical detection device as claimed in claim 3, wherein at least one of the first axicon lens or the second axicon lens is movable relative to the other of the first axicon lens or the second axicon lens.

6. The optical detection device as claimed in claim 3, further comprising a third axicon lens for focusing the annular illumination pattern onto the sample to illuminate the portion of the sample;
wherein a focusing lens is configured to receive the return light from the third axicon lens, the focusing lens further configured to focus the return light to the fiber assembly.

7. The optical detection device as claimed in claim 2, wherein the shaping optics comprises a mask comprising a non-transmissive portion, the non-transmissive portion configured to selectively block a part of the light received by the mask to generate the annular illumination pattern.

8. The optical detection device as claimed in claim 7, further comprising an imaging lens for focusing the annular illumination pattern onto the sample to illuminate the portion of the sample.

9. The optical detection device as claimed in claim 7, further comprising a collimation lens to collimate the light to be received by the mask.

10. The optical detection device as claimed in claim 2, wherein the shaping optics comprises an axicon lens configured to generate the annular illumination pattern and further configured to focus the annular illumination pattern onto the sample to illuminate the portion of the sample.

11. The optical detection device as claimed in claim 10, further comprising a collimation lens to collimate the light to be received by the axicon lens.

12. The optical detection device as claimed in claim 1, further comprising a focusing lens arranged to focus the return light to the fiber assembly.

13. The optical detection device as claimed in claim 1, wherein the detector arrangement comprises a spectrometer for spectrally dispersing the return light for detection.

14. The optical detection device as claimed in claim 1, wherein the detector arrangement comprises a detector to detect the return light.

15. The optical detection device as claimed in claim 1, further comprising a filter for filtering the return light.

16. The optical detection device as claimed in claim 1, further comprising a light source, wherein the optics arrangement is configured to generate the annular illumination pattern based on a light produced by the light source.

17. An optical detection method comprising:
generating an annular illumination pattern;
illuminating a portion of a sample with the annular illumination pattern;

receiving, by a fiber assembly, a return light from the portion of the sample illuminated by the annular illumination pattern and optically coupling the return light for detection; and detecting the return light from the portion of the sample illuminated by the annular illumination pattern;

wherein the fiber assembly comprises a plurality of dead fibers and a plurality of live fibers, wherein the plurality of dead fibers and the plurality of live fibers are arranged in a plurality of concentric patterns at one end of the fiber assembly to receive the return light;

wherein the plurality of live fibers are arranged in a plurality of linear blocks at an opposite end of the fiber assembly;

wherein a number of linear blocks corresponds to a number of concentric patterns; and wherein the live fibers of each concentric pattern are arranged in a respective linear block of the plurality of linear blocks so that each linear block of the plurality of linear blocks corresponds to one concentric pattern.

* * * * *